(12) United States Patent
Makino et al.

(10) Patent No.: US 12,303,890 B2
(45) Date of Patent: May 20, 2025

(54) METHOD OF INTRODUCING LIQUID INTO WELLS

(71) Applicant: TOPPAN Inc., Tokyo (JP)

(72) Inventors: Yoichi Makino, Taito-ku (JP); Yosuke Horiuchi, Taito-ku (JP)

(73) Assignee: TOPPAN Inc., Tokyo (JP)

( * ) Notice: Subject to any disclaimer, the term of this patent is extended or adjusted under 35 U.S.C. 154(b) by 730 days.

(21) Appl. No.: 17/537,650

(22) Filed: Nov. 30, 2021

(65) Prior Publication Data

US 2022/0088598 A1 Mar. 24, 2022

Related U.S. Application Data

(63) Continuation of application No. PCT/JP2020/020925, filed on May 27, 2020.

(30) Foreign Application Priority Data

May 30, 2019 (JP) ................................. 2019-101305

(51) Int. Cl.
*B01L 3/00* (2006.01)

(52) U.S. Cl.
CPC ... *B01L 3/502715* (2013.01); *B01L 3/502707* (2013.01); *B01L 2200/0689* (2013.01); *B01L 2200/12* (2013.01); *B01L 2200/16* (2013.01); *B01L 2300/0663* (2013.01); *B01L 2300/0829* (2013.01)

(58) Field of Classification Search
CPC ........ B01L 3/502715; B01L 3/502707; B01L 2200/0689; B01L 2200/12; B01L 2200/16; B01L 2300/0663; B01L 2300/0829; B01L 2300/0877; B01L 3/502769; C12M 23/12; G01N 35/02; G01N 37/00
See application file for complete search history.

(56) References Cited

U.S. PATENT DOCUMENTS

2011/0212848 A1* 9/2011 Duffy ............... G01N 33/54313
506/15
2016/0333400 A1* 11/2016 Makino ............. B01L 3/502715

FOREIGN PATENT DOCUMENTS

| CN | 103415774 A | 11/2013 |
| CN | 106662599 A | 5/2017 |
| CN | 107109320 A | 8/2017 |
| EP | 3 101 115 A1 | 12/2016 |

(Continued)

OTHER PUBLICATIONS

Extended European Search Report issued on Jul. 1, 2022 in European Patent Application No. 20813025.2, 6 pages.

(Continued)

*Primary Examiner* — John McGuirk
(74) *Attorney, Agent, or Firm* — Oblon, McClelland, Maier & Neustadt, L.L.P.

(57) ABSTRACT

A method of replacing liquids including introducing a second liquid into a fluidic device which includes a substrate having wells formed on a surface thereof, the wells including openings which accommodate a first liquid including a surfactant and are sealed with a first sealing solution applied on the surface of the substrate, where the introducing includes supplying the second liquid to the surface such that the first sealing solution is replaced with the second liquid, and that the second liquid is introduced into the wells.

20 Claims, 20 Drawing Sheets

(56) References Cited

FOREIGN PATENT DOCUMENTS

| JP | 2014-503831 A | 2/2014 |
|----|---------------|--------|
| JP | 5551798 B2 | 7/2014 |
| WO | WO 2019/098301 A1 | 5/2019 |

OTHER PUBLICATIONS

Moriizumi et al., "Hybrid cell reactor system from *Escherichia coli* protoplast cells and arrayed lipid bilayer chamber device", Scientific Reports, 2018, vol. 8, No. 1, pp. 1-13, XP055766931.
International Search Report issued Aug. 18, 2020 in PCT/JP2020/020925, filed May 27, 2020, 7 pages (with English Translation).
Kim et al., "Large-scale femtoliter droplet array for digital counting of single biomolecules", Lab Chip, 12, pp. 4986-4991, 2012.
Watanabe et al., "High-throughput formation of lipid bilayer membrane arrays with an asymmetric lipid composition", Scientific Reports, vol. 4, Article No. 7076, pp. 1-6, 2014.
Combined Chinese Office Action and Search Report issued Oct. 11, 2024, in corresponding Chinese Patent Application No. (with English Translation and English Translation of Category of Cited Documents) citing documents 15-17 therein, 13 pages.

\* cited by examiner

METHOD OF INTRODUCING LIQUID INTO WELLS

CROSS-REFERENCE TO RELATED APPLICATIONS

The present application is a continuation of International Application No. PCT/JP2020/020925, filed May 27, 2020, which is based upon and claims the benefits of priority to Japanese Application No. 2019-101305, filed May 30, 2019. The entire contents of all of the above applications are incorporated herein by reference.

BACKGROUND OF THE INVENTION

Field of the Invention

The present invention relates to a method of introducing liquid into wells.

Discussion of the Background

Early detection of disease and prediction of the effects of medication may be performed by quantitatively detecting a target molecule in a biological sample. Conventionally, protein quantification has been performed by enzyme-linked immunosorbent assay (ELISA) or the like, and nucleic acid quantification has been performed by the real-time PCR method or the like.

In recent years, there is an increasing need for detecting a target molecule more accurately for the purpose of, for example, detecting disease earlier. For example, PTL 1, PTL 2, and NPL 1 disclose techniques for performing an enzyme reaction in a large number of micro compartments as techniques for accurately detecting a target molecule. These techniques are called digital quantification.

In digital quantification, a sample solution is divided into a large number of micro compartments. Then, a signal from each micro compartment is binarized, and the number of target molecules is measured by determining only whether the target molecule is present or not. The digital quantification can significantly improve the detection sensitivity and the quantitativeness compared with conventional methods such as ELISA, real-time PCR method and the like.

The digital quantification technology is widely used not only for the above diagnostic application, but also for an application in which a large number of target molecules are separated from each other and analyzed. For example, in NPL 2 and the like, the digital quantification technology is used for functional analysis of transmembrane proteins.

PTL 1: JP 5551798 B
PTL 2: JP 2014-503831 T
NPL 1: Kim S. H., et al., Large-scale femtoliter droplet array for digital counting of single biomolecules, Lab on a Chip, 12 (23), 4986-4991, 2012.
NPL 2: Rikiya Watanabe, et al., High-throughput formation of lipid bilayer membrane arrays with an asymmetric lipid composition, Scientific Reports volume 4, Article number: 7076, 2014.

SUMMARY OF THE INVENTION

According to an aspect of the present invention, a method of replacing liquids includes introducing a second liquid into a fluidic device which includes a substrate having wells formed on a surface thereof, the wells including openings which accommodate a first liquid including a surfactant and are sealed with a first sealing solution applied on the surface of the substrate, where the introducing includes supplying the second liquid to the surface such that the first sealing solution is replaced with the second liquid, and that the second liquid is introduced into the wells.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 21A and 20B are microscopic images showing results obtained using Example 3.

DESCRIPTION OF THE EMBODIMENTS

Figure 1:
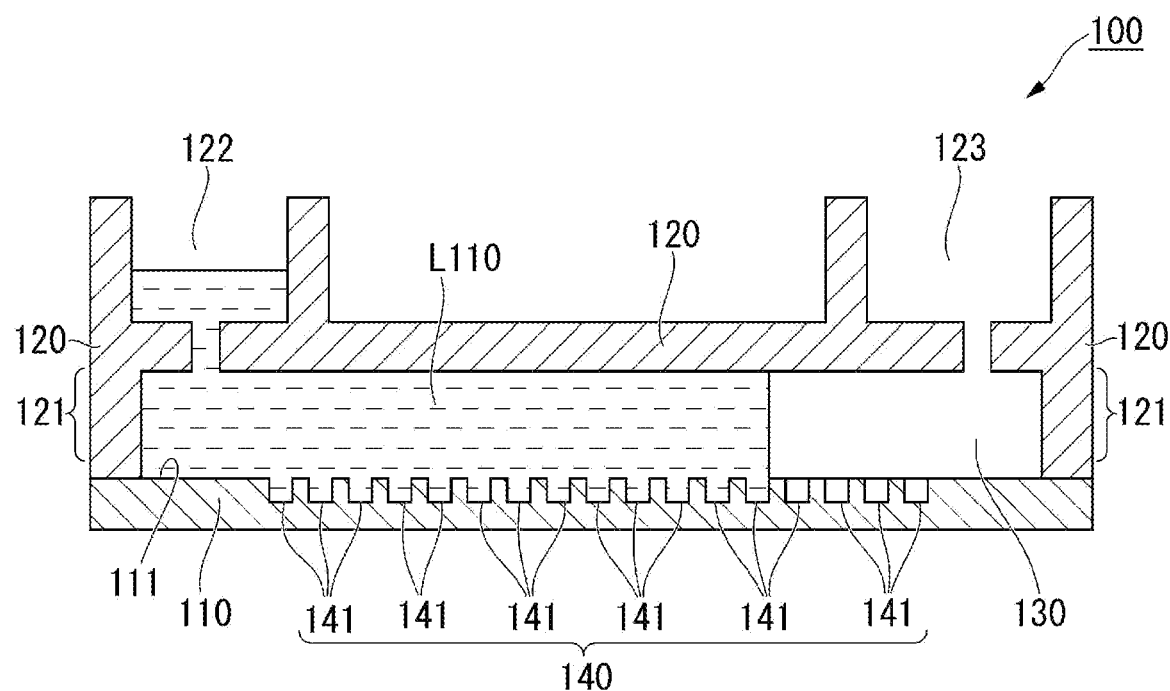
FIG. 1 is a schematic cross-sectional view illustrating an example of a fluidic device.

The embodiments will now be described with reference to the accompanying drawings, wherein like reference numerals designate corresponding or identical elements throughout the various drawings.

With reference to the drawings as appropriate, embodiments of the present invention will be described in detail. Throughout the drawings, the same or corresponding parts are denoted by the same or corresponding reference numerals, and duplicated description is omitted. Further, some of the dimensions in the drawings are exaggerated for convenience of illustration, and are not necessarily to scale.

<Method of Introducing Liquid into Wells>

An embodiment of the present invention provides a method of introducing a second liquid into wells in a fluidic device which includes a substrate and a plurality of the wells, the wells being open to a first surface of the substrate and accommodating a first liquid containing a surfactant, and openings of the wells being sealed with a first sealing solution supplied onto the first surface, the method including: introducing the second liquid onto the first surface, whereby the first sealing solution is replaced with the second liquid.

According to the method of the present embodiment, liquid in the individually sealed micro compartments can be replaced. Accordingly, in digital quantification technology, for example, after an analysis result is obtained using a reaction reagent contained in a first liquid introduced into the micro compartments, the liquid in the micro compartments is replaced with a second liquid so that another analysis can be performed using a reaction reagent contained in the second liquid.

(Fluidic Device)

First, a fluidic device that can be used in the method of the present embodiment will be described. FIG. 1 is a schematic cross-sectional view illustrating an example of a fluidic device. As shown in FIG. 1, a fluidic device 100 includes a substrate 110, and a cover member 120 disposed to face a first surface 111 of the substrate 110. The cover member 120 has a projection 121. The distal end of the projection 121 is in contact with the substrate 110. In the fluidic device 100, a plurality of wells 141, forming a well array 140, are integrally formed on the first surface 111 of the substrate 110. The first surface 111 faces the cover member 120. The cover member 120 may be welded or bonded to the substrate 110.

The wells 141 are open to a surface of the substrate 110. Although the shape, size, and arrangement of the wells 141 are not specifically limited, it is preferred that one target molecule is introduced into each well 141. The wells 141 are preferably microwells having a small volume. For example, each well 141 may have a volume of approximately 10 fL to 100 pL. In the fluidic device 100, the plurality of wells 141 having the same shape and the same size constitute the well array 140. The expression "the same shape and the same size" refers to the shape and the volume being the same to the extent required for digital quantification, and a variation approximately within a manufacturing error may be accepted.

The well 141 may have a diameter of, for example, approximately 1 to 30 μm. The well 141 may have a depth of, for example, approximately 1 to 30 μm. Further, the arrangement of the wells 141 is not specifically limited. For example, the wells 141 may be arranged in a triangular lattice or a square lattice shape, or randomly arranged.

In the fluidic device 100, since the projection 121 is provided, a space is formed between the first surface 111 and the cover member 120. The space constitutes a flow path 130. The flow path 130 functions as a path for supplying a first liquid, a first sealing solution, a second liquid, and a second sealing solution, which will be described later. That is, the first liquid, the first sealing solution, the second liquid, and the second sealing solution are introduced into the fluidic device 100 through the flow path 130.

Although the shape, structure, volume, and the like of the flow path 130 are not specifically limited, the height of the flow path 130 (that is, a distance between the first surface 111 of the substrate 110 and a surface of the cover member 120 facing the substrate 110) may be, for example, 100 μm or less.

The projection 121 may be molded integrally with the cover member 120. For example, the cover member 120 can be formed as a plate shape having the projection 121 by molding a thermoplastic resin fluid using a mold. In addition, an inlet port 122 and a discharge port 123 for a reagent may also be formed on the cover member 120.

When the cover member 120 includes the projection 121, the cover member 120 and the substrate 110 are stacked with the projection 121 being in contact with the surface 111 of the substrate 110 to which the wells 141 are open. A space thus formed between the cover member 120 and the substrate 110 is provided as the flow path 130. The cover member 120 and the substrate 110 may be welded to each other by laser welding or the like.

(First Modification of Fluidic Device)

Figure 7:
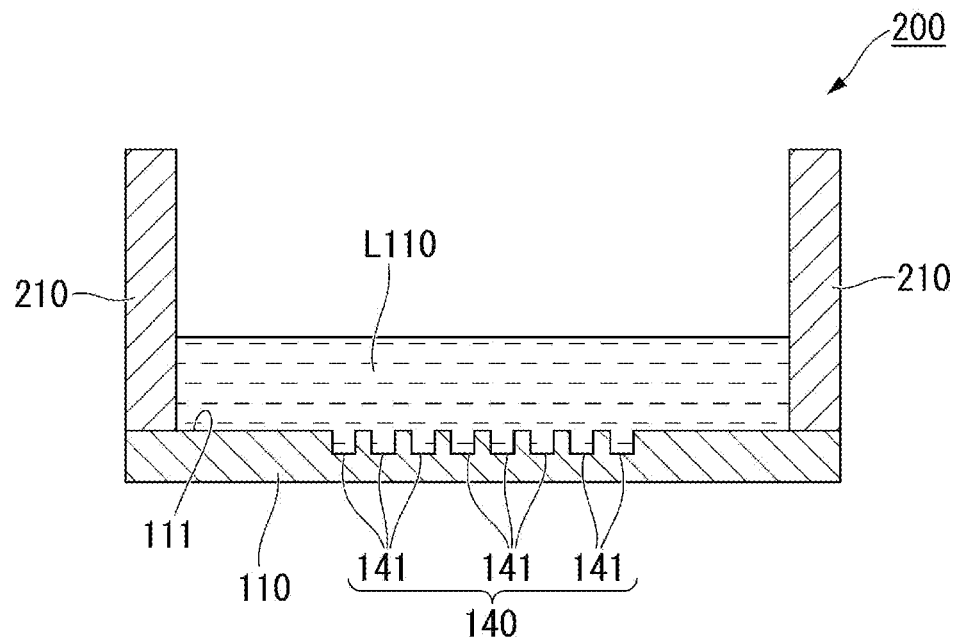
FIG. 7 is a schematic cross-sectional view illustrating an example of a fluidic device.

A fluidic device used for the method of the present embodiment is not limited to the above fluidic device 100. FIG. 7 is a schematic cross-sectional view illustrating an example of a fluidic device. As shown in FIG. 7, a fluidic device 200 includes the substrate 110 and a wall member 210. In the fluidic device 200, the well array 140 is molded integrally with the substrate 110 on the first surface 111 of the substrate 110. The well array 140 includes a plurality of wells 141.

The fluidic device 200 differs from the above fluidic device 100 mainly in that it does not include the cover member 120. Accordingly, the fluidic device 200 does not include a flow path.

(Second Modification of Fluidic Device)

In the above fluidic device 100, the cover member 120 and the projection 121 are integrally molded. However, the cover member 120 and the projection 121 may also be molded as separate members.

Further, in the above fluidic device 100 and the fluidic device 200, the well array 140 is molded integrally with the substrate 110 on the first surface 111 of the substrate 110. However, the well array may not necessarily be molded integrally with the substrate 110. For example, a well array 140 molded separately from the fluidic device may be disposed on the substrate 110 of the fluidic device. Alternatively, a resin layer may be laminated on a surface of the substrate 110 to form a well array on the resin layer by etching or the like.

(Materials of Fluidic Device)

The substrate 110 is formed using a resin, for example. Although the type of the resin is not specifically limited, it is preferred that the resin is resistant to the first liquid, the second liquid, and the sealing solutions. Further, when a signal to be detected is fluorescence, it is preferred that the resin has low autofluorescence. Examples of the resin may include, but are not limited to, a cycloolefin polymer, a cycloolefin copolymer, silicone, polypropylene, polycarbonate, polystyrene, polyethylene, polyvinyl acetate, a fluororesin, an amorphous fluororesin, and the like.

A plurality of wells 141 may be formed on the first surface 111 located on one side of the substrate 110 in the thickness direction. The wells may be formed using a resin by injection molding, thermal imprinting, optical imprinting, or the like.

Alternatively, for example, a fluororesin may be laminated on the substrate 110 to form a well array on the fluororesin by etching or the like. As the fluororesin, for example, CYTOP (registered trademark) (Asahi Glass Co., Ltd.) or the like may be used.

When the fluidic device includes the cover member 120, the material of the cover member 120 is preferably a resin having low autofluorescence, and may be, for example, a thermoplastic resin such as a cycloolefin polymer or a cycloolefin copolymer.

Further, the cover member 120 may also be formed of a material that does not transmit light of a wavelength near the wavelength detected in fluorescence observation of a signal, or a material that only partially transmits light. For example, the cover member 120 may be formed of a thermoplastic resin to which carbon or metal particles are added.

First Embodiment

As described above, a method of the present embodiment is a method of introducing a second liquid into wells in a fluidic device which includes a substrate and a plurality of the wells, the wells being open to a first surface of the substrate and accommodating a first liquid containing a surfactant, and openings of the wells being sealed with a first sealing solution supplied onto the first surface, the method including: introducing the second liquid onto the first surface, whereby the first sealing solution is replaced with the second liquid.

With reference to FIGS. 1 to 6 as appropriate, a method of a first embodiment will be described by using an example in which the fluidic device 100 is used.

<Introduction of First Liquid>

First, as shown in FIG. 1, a first liquid L110 is introduced through the inlet port 122 of the fluidic device 100 into the flow path 130. The first liquid L110 includes, for example, biological samples or environmental samples. Examples of the biological samples may include, but are not limited to, serum, plasma, urine, cell culture solution, and the like. In addition, examples of the environmental samples may include river water, factory wastewater, and the like.

The biological samples and environmental samples may contain target molecules to be detected. Alternatively, the biological samples and environmental samples may not contain target molecules to be detected. Examples of the target molecules include DNA, RNA, proteins, viruses, cells, specific compounds, and the like. The RNA may be miRNA, mRNA, or the like. Further, the cells may be bacteria, yeast, animal cells, plant cells, insect cells, or the like.

The first liquid L110 may contain a reaction reagent for detecting a target molecule. Examples of the reaction reagent include buffer substances, enzymes, substrates, antibodies, antibody fragments, and the like. The enzyme is selected according to the content of biochemical reaction. For example, when the target molecule is a nucleic acid, the enzyme is selected to perform a biochemical reaction such as an enzyme reaction with a template nucleic acid associated with the target molecule. The biochemical reaction to the template nucleic acid is, for example, a reaction in which signal amplification occurs in the presence of a template nucleic acid. The reaction reagent is selected according to the detection reaction to be employed. Specific examples of the detection reaction include an invasive cleavage assay (ICA) method, loop-mediated isothermal amplification (LAMP) method (registered trademark), 5'→3' nuclease method (TaqMan (registered trademark)), fluorescent probe method, and the like.

The first liquid L110 contains a surfactant. Examples of the surfactant include Triton-X100 (also known as polyethylene glycol mono-4-octylphenyl ether (n=approx. 10)), sodium dodecyl sulfate, Nonidet P-40 (also known as octylphenoxy poly(ethyleneoxy)ethanol), Tween20 (also known as polyoxyethylene sorbitan monolaurate), and the like.

The concentration of the surfactant is preferably 0.001 v/v % or more and 1.0 v/v % or less relative to the total volume of the first liquid L110, more preferably 0.005 v/v % or more and 0.5 v/v % or less, and still more preferably 0.01 v/v % or more and 0.1 v/v % or less. When the concentration of the surfactant is 0.001 v/v % or more relative to the total volume of the first liquid L110, replacement with the second liquid L410 can be easily performed. When the concentration of the surfactant is 1.0 v/v % or less relative to the total volume of the first liquid L110, the influence on the reaction in the subsequent detection of target molecule can be minimized.

The first liquid L110 supplied into the flow path 130 is accommodated in the wells 141. Accordingly, the reaction reagent, the surfactant, and target molecules, if present, are introduced into the wells 141.

Although the number of target molecules introduced into each well 141 is not specifically limited, it is preferred that 1 or less, that is, 0 or 1 target molecule is introduced into each well 141. Accordingly, the target molecule can be detected in units of one piece, that is, digital quantification can be performed. The target molecule is not necessarily introduced into every well 141 of the well array 140.

A means for introducing target molecules into the wells 141 is not specifically limited, and an appropriate means for the selected target molecule can be used. For example, target molecules may precipitate by their own weight in the fluidic device (specifically, in the flow path), and be distributed into the wells 141. Alternatively, a carrier (that is, capture substance) for capturing target molecules may be used. The target molecules that are unlikely to precipitate by their own weight can be bound to the capture substances when they are supplied. Further, the capture substances can be immobilized to the wells 141 in advance so as to capture target molecules that are supplied. Accordingly, the target molecules can be introduced into the wells at improved efficiency.

The step of binding the capture substances to the target molecules can be performed at any time. For example, the step may be performed by bringing the target molecules and the capture substances into contact with each other in a sample tube before the target molecules are introduced into the wells 141. Alternatively, the target molecules may be introduced into the wells after the capture substances are introduced into the wells 141 so that the capture substances and the target molecules are in contact with other in the wells.

The capture substance is a substance capable of capturing target molecules. The capture substance may be, for example, a conjugate of a solid phase and a specific binding substance for the target molecule.

The solid phase may be particles, films, substrates, or the like. Further, the specific binding substance for the target molecule may be one or more. For example, three, four, or five or more specific binding substances may be used.

The particles are not specifically limited, and may be polymer particles, magnetic particles, glass particles, or the like. Preferably, the particles are subjected to a surface treatment in order to avoid nonspecific adsorption. Further, in order to immobilize the specific binding substance, particles having a functional group such as a carboxyl group on the surface are preferred. More specifically, a product "Magnosphere LC300" manufactured by JSR Corporation or the like can be used as the particles.

Alternatively, for example, when a virus is used as the target molecule, a cell to which the virus can be attached (that is, a cell having a virus receptor) can be used as the capture substance.

Examples of the specific binding substance in the capture substance include antibodies, antibody fragments, aptamers, and the like. Examples of the antibody fragment include Fab, F(ab)$_2$, Fab', single chain antibodies (scFv), disulfide stabilized antibodies (dsFv), dimeric V region fragments (Diabody), peptides including CDR, and the like. The antibody may be a monoclonal antibody or a polyclonal antibody. Alternatively, the antibody may be a commercially available antibody.

When the target molecule contains a sugar chain, the specific binding substance may be a lectin. Further, when the target molecule contains a lipid membrane, the specific binding substance may be a substance that binds to the lipid membrane. Examples of the substance that binds to lipid membrane include hydrocarbons such as hexanediol and membrane proteins such as transmembrane proteins. The membrane proteins may be, for example, α-hemolysin.

The method of immobilizing the specific binding substance to the solid phase is not limited, and it is possible to use a method using physical adsorption, a method using chemical bonding, a method using avidin-biotin binding, a method of using a bond between protein G or protein A to an antibody, or the like. As the method by physical adsorption, there is a method of immobilizing a specific binding substance to the particle surface by hydrophobic interaction or electrostatic interaction. As the method by chemical bonding, there is a method using a crosslinking agent. For example, in the case where the surface of the particle has a hydroxyl group, the carboxyl group of the specific binding substance is allowed to react with a crosslinking agent to obtain an active ester, and then the hydroxyl group and the ester group are allowed to react, whereby the specific binding substance can be immobilized to the particle surface. It is also preferable to provide a spacer between the specific binding substance and the particle surface so as not to inhibit the recognition ability of the specific binding substance to recognize the target molecule.

When a capture substance is used to introduce target molecules into the wells 141, it is preferred that conjugates of the capture substances and the target molecules are formed under the condition that each capture substance captures 0 or 1 target molecule. Furthermore, each well 141 is preferably configured to accommodate 0 or 1 capture substance. Thus, digital quantification can be performed.

<Introduction of Sealing Solution>

Figure 2:
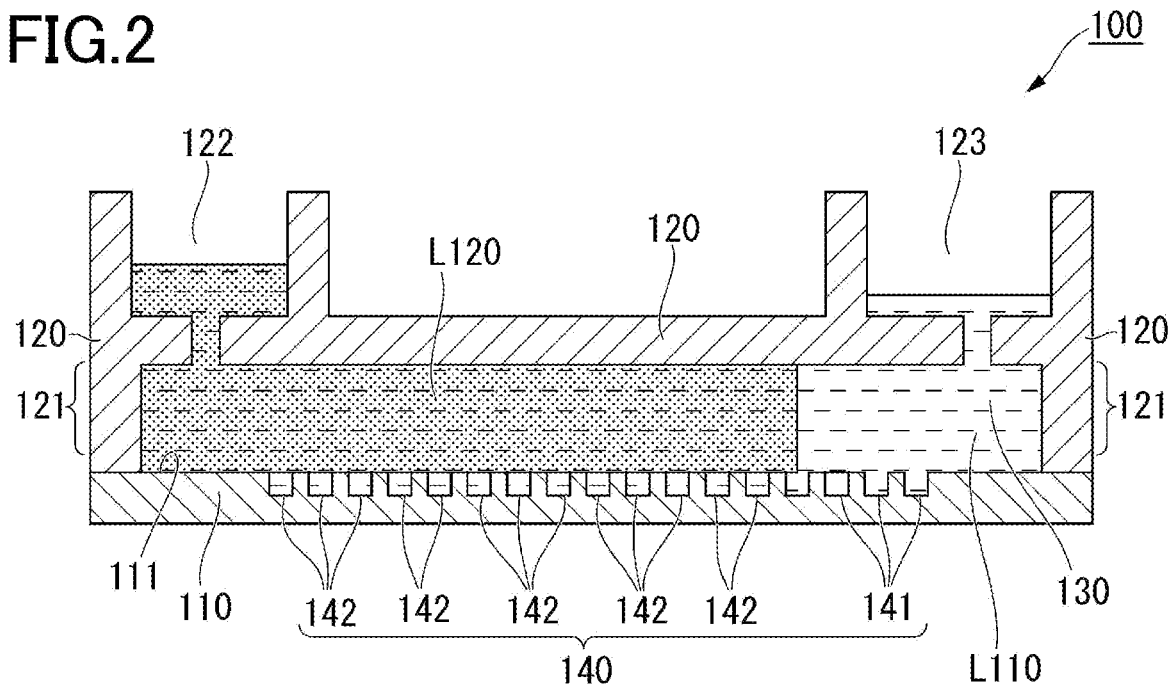
FIG. 2 is a schematic cross-sectional view illustrating an example of a fluidic device.
Figure 3:
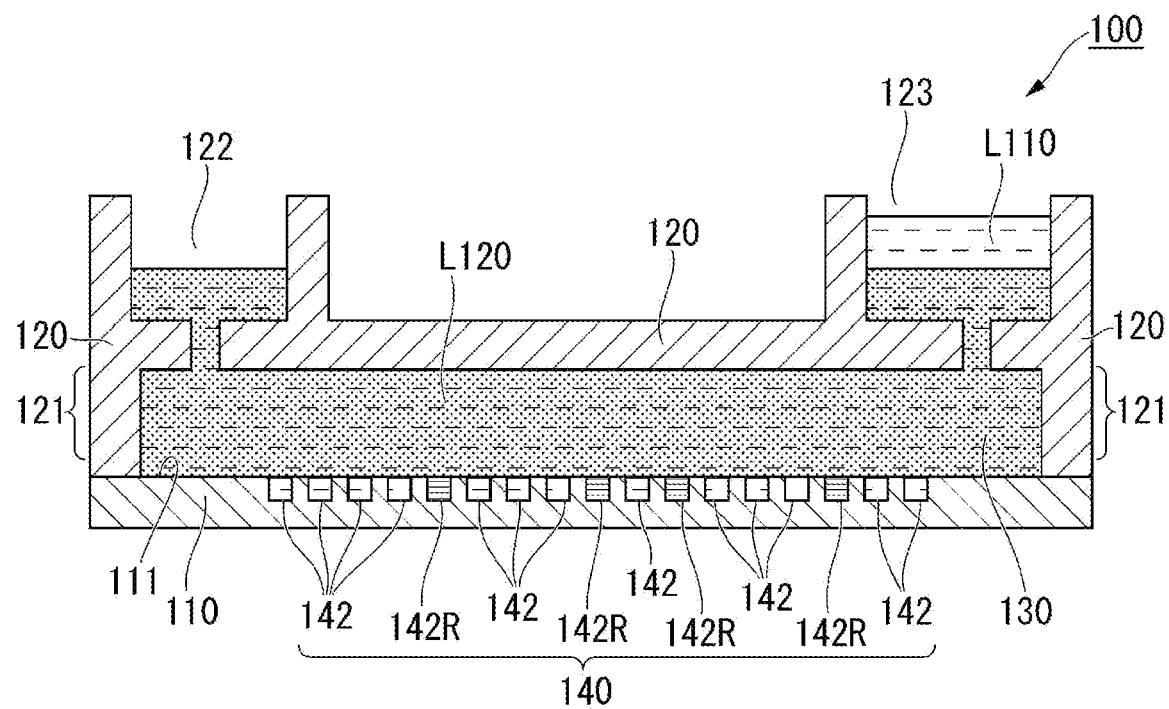
FIG. 3 is a schematic cross-sectional view illustrating an example of a fluidic device.

Then, as shown in FIGS. 2 and 3, a first sealing solution L120 is introduced through the inlet port 122 into the flow path 130.

Due to the first sealing solution, the liquid which has been introduced into the plurality of wells 141 can be individually sealed, forming liquid droplets (microdroplets). Accordingly, the liquid in each well can be prevented from being mixed with one another. The first sealing solution is preferably an oily solution, and more preferably an oil. Examples of the oil include fluorine-based oil, silicone-based oil, hydrocarbon-based oil, and a mixture thereof. More specifically, oil manufactured by Sigma under the product name "FC-40" or the like can be used. FC-40 (CAS Number: 86508-42-1) is a fluorinated aliphatic compound having a specific weight of 1.85 g/mL at 25° C.

The first sealing solution L120 supplied to the flow path 130 flushes out and replaces the first liquid L110 which has been introduced into the flow path 130 and is not accommodated in the wells 141. As a result, the plurality of wells 141 are individually sealed by the first sealing solution L120, whereby the wells 141 are provided as independent reaction spaces (micro compartments 142).

As the flow path 130 is filled with the first sealing solution L120, excess first sealing solution L120 is discharged through the discharge port 123. FIG. 3 illustrates that all the wells 141 of the well array 140 are sealed with the first sealing solution L120 and form sealed wells (micro compartments) 142.

Alternatively, the first liquid L110 may contain lipids dissolved therein. After the first sealing solution L120 is supplied into the flow path 130, a liquid containing lipids may be again supplied into the flow path 130 to form a lipid bilayer at the openings of the wells 141. Thus, the plurality of wells 141 are individually sealed with the lipid bilayer, whereby sealed wells 142 are formed. Examples of the lipid forming the lipid bilayer include, but are not limited to, 1,2-dioleoyl-sn-glycero-3-phosphoethanolamine (DOPE), 1,2-dioleoyl-sn-glycero-3-phosphoglycerol (DOPG), and a mixture thereof.

<Detection of Target Molecules>

Target molecules can be detected by using a reaction of a reaction reagent contained in the first liquid L110. For example, a signal amplification reaction may be performed in the sealed wells 142. In other words, a reaction step is performed in which a signal is amplified to a level at which the signal is observable so that a signal derived from a reaction reagent can be detected in the wells 142. Examples of the signal include fluorescence, color development, potential change, pH change, and the like.

The signal amplification reaction is, for example, an enzymatic reaction. As an example, the signal amplification reaction is an isothermal reaction in which, in a state in which the first liquid L110 containing an enzyme for signal amplification is accommodated in the wells 142, the fluidic device 100 is maintained at a constant temperature condition for a predetermined period of time so that a desired enzyme activity is obtained. As a specific example, an ICA reaction can be used as the signal amplification reaction. In this case, the wells 142 accommodate the ICA reaction reagent and a nucleic acid as a target molecule. When the target molecule is accommodated in the wells 142 as a result of the enzymatic reaction, a fluorescent substance is released from a quencher, whereby a specified fluorescence signal is emitted corresponding to the excitation light. In FIG. 3, reference symbol 142R indicates a well in which a target molecule is accommodated and a signal is emitted.

<Introduction of Second Liquid>

Figure 4:
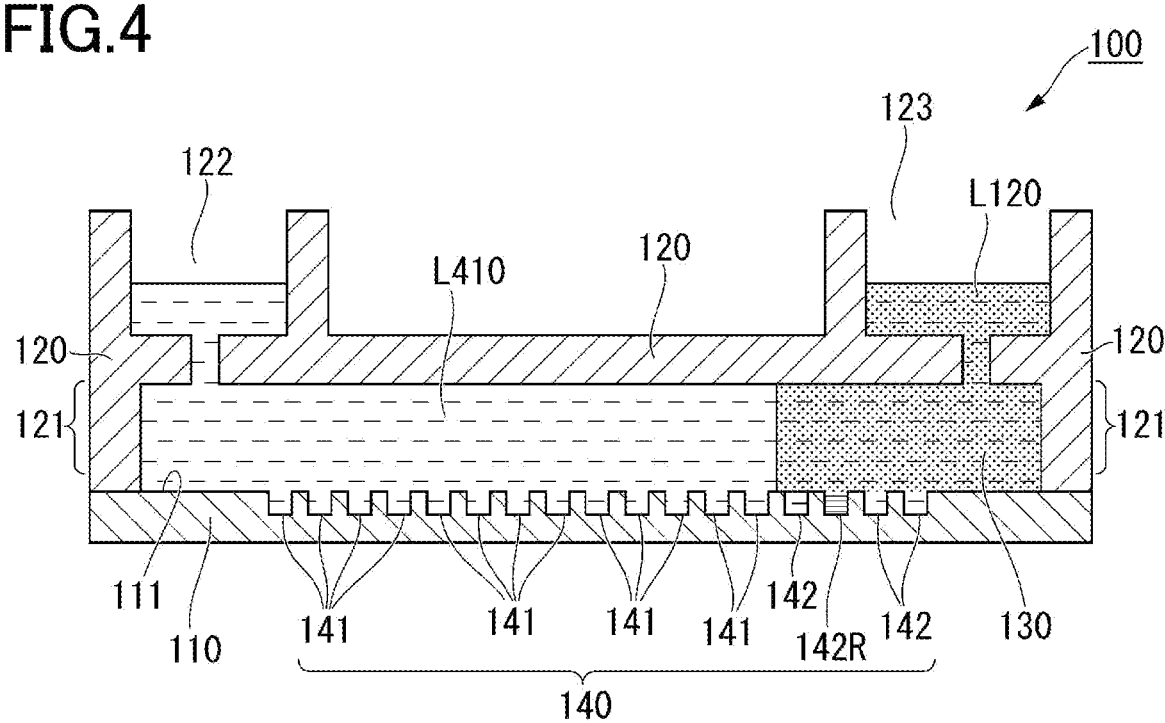
FIG. 4 is a schematic cross-sectional view illustrating an example of a fluidic device.

Then, as shown in FIG. 4, a second liquid L140 is introduced through the inlet port 122 into the flow path 130. As a result, the second liquid L410 flushes out the first sealing solution L120, and is introduced into the wells 141. Although it is preferred that the first sealing solution L120 is completely replaced with the second liquid L410 and removed, the first sealing solution L120 may be partially left as long as the second liquid L410 is introduced into the wells 141.

Conventionally, it has been thought that liquid in the wells 142 sealed with a sealing solution cannot be replaced. However, the inventors have found that, according to the method of the present embodiment described later in the examples, the second liquid L410 can be introduced into the wells 142 which are sealed with the first sealing solution L120.

The second liquid L410 may contain a surfactant, or may not contain a surfactant. When the second liquid L410 contains a surfactant, the type and concentration of the surfactant may be the same as the surfactant of the first liquid L110.

Similarly to the first liquid L110, the second liquid L410 may also contain a reaction reagent for detecting target molecules. Examples of the reaction reagent may be the same as those that can be contained in the first liquid L110 described above, but the reagent is preferably different from that of the first liquid L110. Accordingly, a reaction different from that by the reaction reagent contained in the first liquid L110 can be performed.

The second liquid L410 supplied to the flow path 130 flushes out and replaces the first sealing solution L120 which has been introduced into the flow path 130. This releases the sealing of the individually sealed wells 142, and provides unsealed wells 141. Further, the second liquid L410 is introduced into the wells 141 in which the first liquid L110 is accommodated.

In the method of the first embodiment, it is preferred that the affinity between the first surface 111 and the sealing solution L120 is substantially the same as that between the first surface 111 and the second liquid L410, or lower than that between the first surface 111 and the second liquid L410. Accordingly, as the second liquid L410 is introduced, the second liquid L410 can easily flush out the first sealing solution L120 to thereby release the sealing of the wells 142.

Examples of the case where the affinity between the first surface 111 and the first sealing solution L120 is substantially the same or lower than the affinity between the first surface 111 and the second liquid L410 include a combination in which the first surface 111 is made of a cycloolefin polymer, the first liquid L110 and the second liquid L410 contain water as a main component, and the first sealing solution L120 is a fluorine-based oil.

In the present specification, the liquid containing water as a main component means that the water content in the liquid is 50 mass % or more, for example, 60 mass % or more, 70 mass % or more, 80 mass % or more, 90 mass % or more, 95 mass % or more, or 98 mass % or more. Further, the fluorine-based oil may be, for example, oil manufactured by Sigma under the product name "FC-40" or the like.

Since the first liquid L110 contains a surfactant, the second liquid L410 is introduced into the unsealed wells 141. As a result, liquid in the wells 141 can be replaced with the second liquid L410. That is, after the first liquid L110 containing a surfactant is introduced into the wells 141 and the first liquid L110 is then sealed with the first sealing solution L120, the second liquid L410 is introduced so that liquid in the wells 141 can be replaced with the second liquid L410.

After the second liquid L410 is introduced into the wells 141, at least part of the components contained in the first liquid L110 may remain in the wells 141. For example, while a target molecule contained in the first liquid L110 is bound to the capture substance, the capture substance may remain in the wells 141. That is, at least part of the components contained in the first liquid L110 held by the capture substance (carrier) may remain in the wells 141. In this case, the second liquid L410 is present in the wells 141 together with the capture substance and the target molecule.

Alternatively, for example, while a target molecule contained in the first liquid L110 is bound to the capture substance, and an antibody against the target molecule contained in the first liquid L110 is further bound to the target molecule, the capture substance may remain in the wells 141. In this case, the second liquid L410 is present in the wells 141 together with the capture substance, the target molecule, and the antibody bound to the target molecule.

The first liquid L110 and the second liquid L410 are preferably miscible with each other. When the first liquid L110 and the second liquid L410 are miscible with each other, liquid in the wells 141 is efficiently replaced. The term miscible herein refers to that, when the first liquid L110 and the second liquid L410 are mixed with each other, a homogeneous solution or dispersion is formed without being separated into layers.

When the flow path 130 is filled with the second liquid L410, an excess second liquid L410 is discharged through the discharge port 123.

<Introduction of Sealing Solution>

Figure 5:
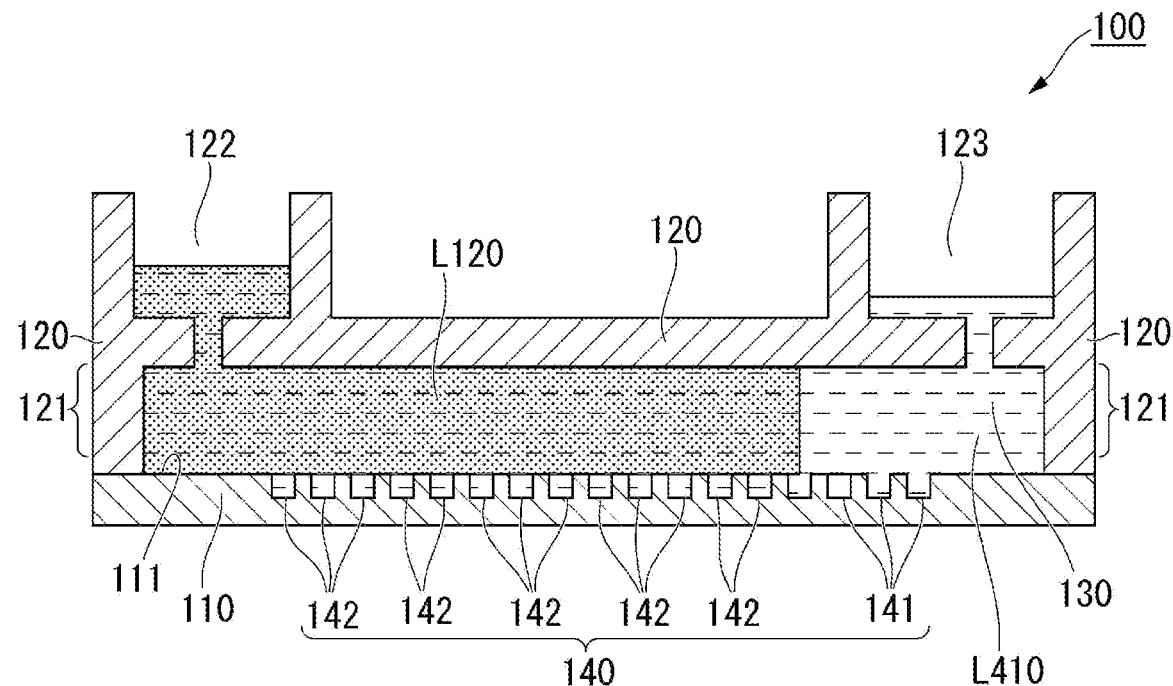
FIG. 5 is a schematic cross-sectional view illustrating an example of a fluidic device.

After a step of introducing the second liquid L410, a step of introducing a second sealing solution L120 into the fluidic device 100 may be further performed. The second sealing solution may be the same as the above first sealing solution, or different from the first sealing solution. Specifically, as shown in FIG. 5, the second sealing solution L120 may be again introduced through the inlet port 122 into the flow path 130.

As a result, the openings of the plurality of wells 141 are sealed with the second sealing solution L120 which is supplied onto the first surface 111 with the second liquid L410 or a mixture of the first liquid L110 and the second liquid L410 being accommodated in the wells 141, whereby the respective wells 141 are provided as independent reaction spaces (micro compartments 142).

Figure 6:
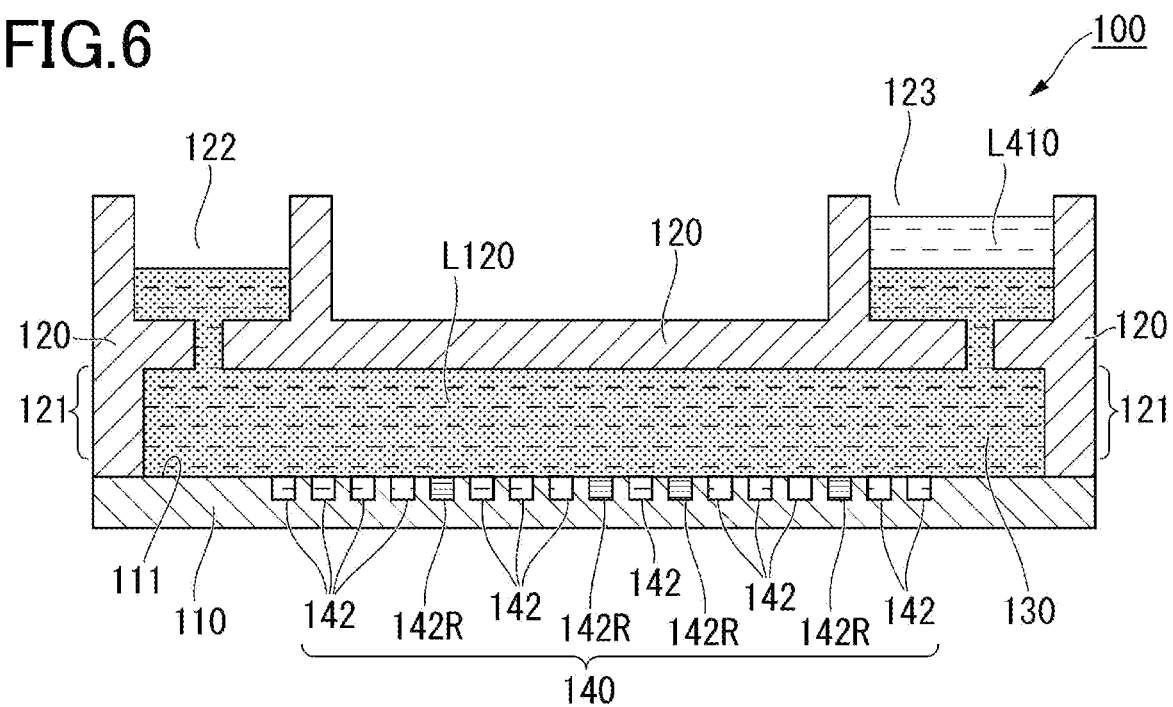
FIG. 6 is a schematic cross-sectional view illustrating an example of a fluidic device.

As the flow path 130 is filled with the second sealing solution L120, excess second sealing solution L120 is discharged through the discharge port 123. FIG. 6 illustrates that all the wells 141 of the well array 140 are sealed with the second sealing solution L120 and form sealed wells (micro compartments) 142.

Alternatively, the second liquid L410 may contain lipids dissolved therein. After the second sealing solution L120 is supplied into the flow path 130, a liquid containing lipids may be again supplied into the flow path 130 to form a lipid bilayer at the openings of the wells 141. Thus, the plurality of wells 141 are individually sealed with the lipid bilayer, whereby sealed wells 142 are formed. Examples of the lipids forming the lipid bilayer include those described above.

<Detection of Target Molecules>

Target molecules can be detected by using a reaction of a reaction reagent contained in the second liquid L410 in the same manner as described above. For example, a signal amplification reaction may be performed in the sealed wells 142. In FIG. 6, reference symbol 142R indicates a well in which a target molecule is accommodated and a signal is emitted as a result of reaction of the reaction reagent.

Second Embodiment

Next, with reference to FIGS. 7 to 11, a method of a second embodiment will be described by using an example in which a fluidic device 200 is used. The method of the second embodiment differs from that of the first embodiment in that the fluidic device does not include a cover member. Further, a first sealing solution and a second sealing solution in the method of the second embodiment differ from the first sealing solution and the second sealing solution in the method of the first embodiment in that they are required to satisfy the specific weight conditions described later.

<Introduction of First Liquid>

First, as shown in FIG. 7, the first liquid L110 is introduced into the fluidic device 200. The first liquid L110 is the same as that described above. As shown in FIG. 7, the first liquid L110 is accommodated in the wells 141. Accordingly, the reaction reagent and target molecules, if present, are introduced into the wells 141. Although the number of target molecules introduced into each well 141 is not specifically limited, it is preferred that 1 or fewer, that is, 0 or 1 target molecule is introduced into each well 141.

<Introduction of Sealing Solution>

Figure 8:
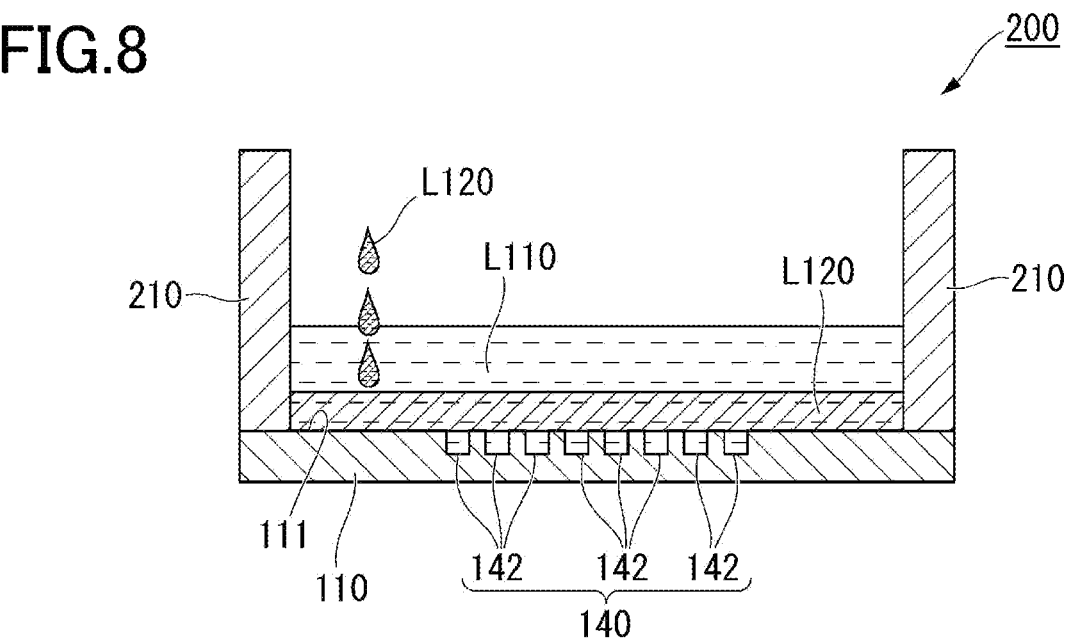
FIG. 8 is a schematic cross-sectional view illustrating an example of a fluidic device.

Then, as shown in FIG. 8, the first sealing solution L120 is introduced into the fluidic device 200. The specific weight of the first sealing solution L120 is larger than the specific weight of the first liquid L110. Accordingly, the first sealing solution L120 precipitates under the first liquid L110, and is in contact with the first surface 111. Thus, a plurality of wells 141, in which the first liquid L110 is accommodated, are individually sealed by the sealing solution L120, forming independent reaction spaces (micro compartments 142).

<Detection of Target Molecules>

Figure 9:
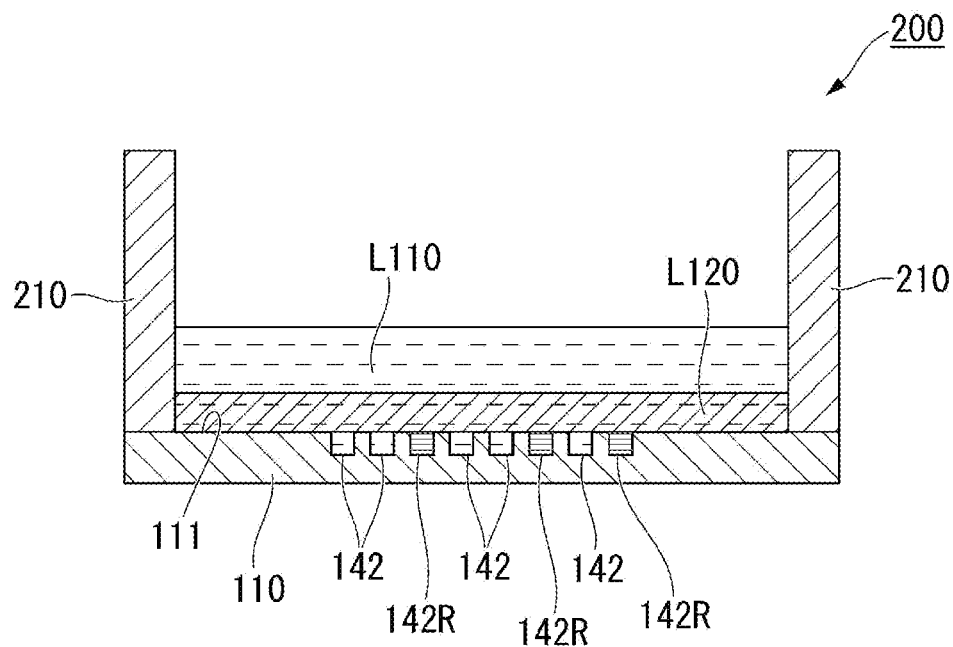
FIG. 9 is a schematic cross-sectional view illustrating an example of a fluidic device.

Then, as shown in FIG. 9, a predetermined reaction may be performed in the wells 142 to observe a generated signal. In FIG. 9, the wells 142R are wells in which a target molecule is accommodated and a signal is detected, and the wells 142 are wells in which no target molecule is accommodated and no signal is detected.

<Introduction of Second Liquid>

Figure 10:
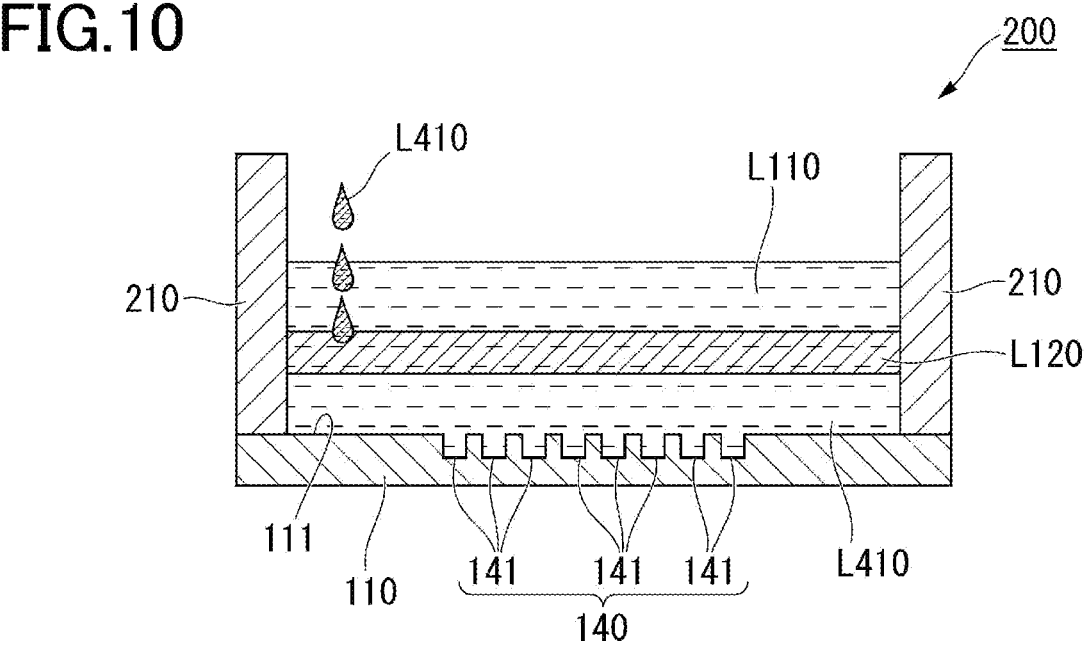
FIG. 10 is a schematic cross-sectional view illustrating an example of a fluidic device.

Then, as shown in FIG. 10, the second liquid L410 is introduced into the fluidic device 200. The specific weight of the second liquid L410 is larger than the specific weight of the first sealing solution L120. Accordingly, the second liquid L410 precipitates under the first sealing solution L120. This releases the sealing of the individually sealed wells 142, and provides unsealed wells 141. Further, the second liquid L410 is introduced into the wells 141. In the wells 141, it is preferred that the first sealing solution L120 is completely replaced with the second liquid L410 and removed. However, the first sealing solution L120 may be partially left as long as the second liquid L410 is introduced into the wells 141.

The second liquid L410 may contain a reaction reagent for detecting a target molecule. Examples of the reaction reagent may be the same as those that can be contained in the first liquid L110 described above, but the reagent is preferably different from that of the first liquid L110. Accordingly, a reaction different from that by the reaction reagent contained in the first liquid L110 can be performed.

In the second embodiment, as in the first embodiment, at least part of the components contained in the first liquid L110 may remain in the wells 141 after the second liquid L410 is introduced into the wells 141.

<Introduction of Sealing Solution>

Figure 11:
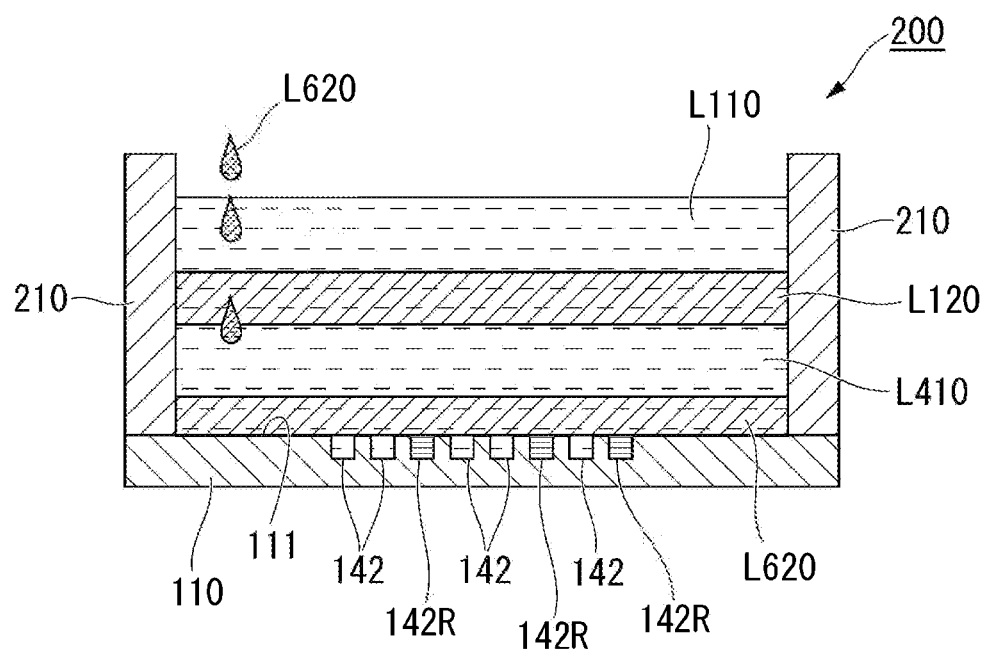
FIG. 11 is a schematic cross-sectional view illustrating an example of a fluidic device.

After a step of introducing the second liquid L410, a step of introducing a second sealing solution L620 into the fluidic device 200 may be further performed. Specifically, as shown in FIG. 11, the second sealing solution L620 is introduced into the fluidic device 200. The specific weight of the second sealing solution L620 is larger than the specific weight of the second liquid L410. Accordingly, the second sealing solution L620 precipitates under the second liquid L410, and is in contact with the first surface 111. Thus, a plurality of wells 141, in which the second liquid L410 or a mixture of the first liquid L110 and the second liquid L410 is accommodated, are individually sealed by the second sealing solution L620, forming independent reaction spaces (micro compartments 142).

FIG. 11 illustrates that all the wells 141 of the well array 140 are sealed with the second sealing solution L620 and form sealed wells (micro compartments) 142.

<Detection of Target Molecules>

Target molecules can be detected by using a reaction of a reaction reagent contained in the second liquid L410 in the same manner as described above. For example, a signal amplification reaction may be performed in the sealed wells 142. In FIG. 11, reference symbol 142R indicates a well in which a target molecule is accommodated and a signal is emitted as a result of reaction of the reaction reagent.

In the method of the second embodiment, it is preferred that the specific weight of the first sealing solution L120 is larger than the specific weight of the first liquid L110, the specific weight of the second liquid L410 is larger than the specific weight of the first sealing solution L120, and the specific weight of the second sealing solution L620 is larger than the specific weight of the second liquid L410. Further, the main component of the first liquid L110 and the second liquid L410 is preferably water. In this case, for example, the specific weight can be adjusted by adding sucrose or the like to the second liquid L410. Further, as the first sealing solution L120 and the second sealing solution L620, materials satisfying the requirements such as specific weight can be appropriately selected from those described above.

In the embodiment described above, the liquid in the micro compartments individually sealed is replaced once. However, according to an aspect of the present invention, the liquid in the individually sealed micro compartments can be replaced twice or more. That is, the liquid can be replaced a desired number of times by repeating an aspect of the present invention.

Specifically, in the above example, the steps of introducing the first liquid L110, sealing by the first sealing solution L120, and introducing the second liquid L410 are sequentially performed. However, these steps are not necessarily sequentially performed. For example, a third liquid may be introduced into the fluidic device 100 between the steps of sealing by the first sealing solution L120 and introducing the second liquid L410, and a third liquid may be sealed in the wells 142 by a third sealing solution. The third liquid may contain a surfactant, or may not contain a surfactant. Even when the third liquid does not contain a surfactant, the liquid containing no surfactant in the wells 141 can be replaced with the second liquid L410 by introducing the second liquid L410 into the fluidic device 100.

The reason for this seems to be that, since a surfactant is introduced into the wells 141 due to introduction of the first liquid L110, the surfactant may remain in the wells 141 or may be attached to an inner wall of the wells 141 even when liquid in the wells 141 is replaced with liquid containing no surfactant. Accordingly, when the second liquid L410 is introduced, liquid in the wells 141 can be replaced with the second liquid L410 due to an effect of the surfactant remaining in the wells 141.

Further, a fourth liquid may be introduced between the steps of sealing by the third sealing solution and introducing the second liquid L410, and a fourth liquid may be sealed in the wells 141 by a fourth sealing solution. The fourth liquid may contain a surfactant, or may not contain a surfactant.

According to an aspect of the present invention, when a plurality of target molecules are included in a sample, for example, when the sample is a cell or the like, the target molecules can be detected in a simplified manner. One example is described below.

A first liquid L110 containing cells and a first reaction reagent is introduced into the wells 141. In this case, the cells are preferably introduced into the wells 141 using capture substances. The capture substances, configured such that cells bound to the capture substances remain in the wells 142 after the second liquid L410 is introduced, are used. For example, capture substances having a sufficiently large mass or capture substances immobilized in the wells 141 may be used.

Then, a first sealing solution is introduced to obtain wells 142, and detection of first target molecules is performed using the first reaction reagent. Further, a second liquid L410 containing a second reaction reagent is introduced into the wells 141 to replace liquid in the wells 141 with the second liquid. Then, a second sealing solution is introduced into the flow path 130 to obtain sealed wells 142. The wells 142 then contain cells bound to the capture substances, and the second liquid L410. Then, detection of second target molecules is performed using the second reaction reagent.

As described above, when a plurality of target substances are included in the sample, the plurality of target substances can be detected in a simplified manner without using a plurality of devices.

EXAMPLES

The present invention will be described in more detail using the examples, but the present invention is not limited to the following examples.
(Production of Fluidic Device)
First, a fluidic device having a structure as shown in FIG. 1 was produced. The fluidic device was produced by adhering a substrate 110 and a cover member 120 to each other with a double-sided tape. The substrate 110, made of a cycloolefin polymer, was formed by injection molding and provided with a well array 140, and the cover member 120, made of a cycloolefin polymer, was colored by adding a carbon black. The double-sided tape functioned as a projection 121, and a height of the flow path 130 (a distance between the first surface 111 of the substrate 110 and a surface of the cover member 120 facing the substrate 110) was 100 µm. Further, the cover member 120 was provided with an inlet port 122 and a discharge port 123. In addition, each well 141 constituting the well array 140 had a diameter of 5 µm and a depth of 3 µm. A volume Vd of each well 141 was 93 fL.
(First Liquid and Third Liquid)
Liquid containing water (AccuGENE Molecular Biology Grade Water (manufactured by LONZA)) as a solvent, 5 µg/ml Redmond Red as a fluorescent reagent, 10 mM Tris-HCl (manufactured by Nippon Gene, pH:8.5) as a buffer, 6.25 mM $MgCl_2$ (manufactured by SIGMA-ALDRICH) as a salt, and 0.1 v/v % Tween 20 (manufactured by SIGMA-ALDRICH) as a surfactant was prepared as the first liquid and the third liquid.
(Second Liquid)
Liquid containing water (AccuGENE Molecular Biology Grade Water (manufactured by LONZA)) as a solvent, 1 µg/ml fluorescein isothiocyanate (hereinafter, FITC) as a fluorescent reagent, 10 mM Tris-HCl (manufactured by Nippon Gene, pH:8.5) as a buffer, 6.25 mM $MgCl_2$ (manufactured by SIGMA-ALDRICH) as a salt, and 0.1 mass % Tween 20 (manufactured by SIGMA-ALDRICH) as a surfactant was prepared as the second liquid.
(Sealing Solution)
Oil (Fluorinert FC-40, manufactured by SIGMA-ALDRICH) was used as the sealing solution.
(Microscopic Observation)
The devices used were as follows.
Microscope: BZ-800 (manufactured by Keyence)
Objective lens: CFI Plan Apochromat Lambda 10× (manufactured by Nikon)
Filter 1: BZ-X filter TexasRed (manufactured by Keyence)
Filter 2: BZ-X filter GFP (manufactured by Keyence)

Example 1

Figure 12A:
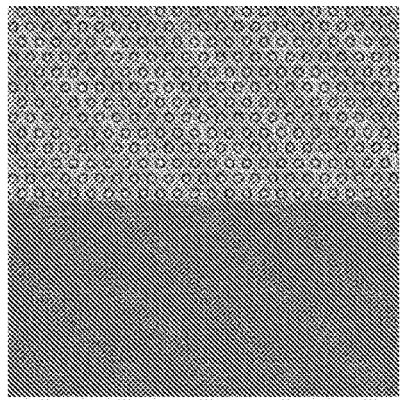
FIGS. 12A and 12B are microscopic images showing results obtained using Example 1.

(Introduction of First Liquid)
20 µL of the first liquid was introduced through the inlet port 122 of the fluidic device.
(Signal Detection 1)
Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of ¼ second. Further, a bright field image of the same field was also captured. FIG. 12A is an observation image of signal detection 1. The upper part of the image is a bright field image, and the lower part is a fluorescence image. As a result, fluorescence was observed across the entire field.
(Introduction of Sealing Solution)
100 µL of the sealing solution was introduced through the inlet port 122 of the fluidic device. As a result, the wells 141 were individually sealed, and sealed wells 142 were formed.

(Signal Detection 2)

Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of 5 seconds. Further, a bright field image of the same field was also captured.

Figure 12B:
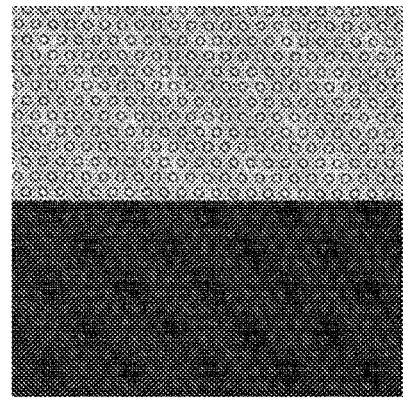

FIG. 12B is an observation image of signal detection 2. The upper part of the image is a bright field image, and the lower part is a fluorescence image. As a result, fluorescence signals corresponding to the positions of the wells 142 were observed. That is, it was found that the first liquid was accommodated in each of the plurality of wells 142.

(Introduction of Second Liquid)

20 µL of the second liquid was introduced through the inlet port 122 of the fluidic device.

(Signal Detection 3)

Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of 5 seconds, and another fluorescence image was captured using the filter 2 at an exposure time of 1/40 second. Further, a bright field image of the same field was also captured.

Figure 13A:
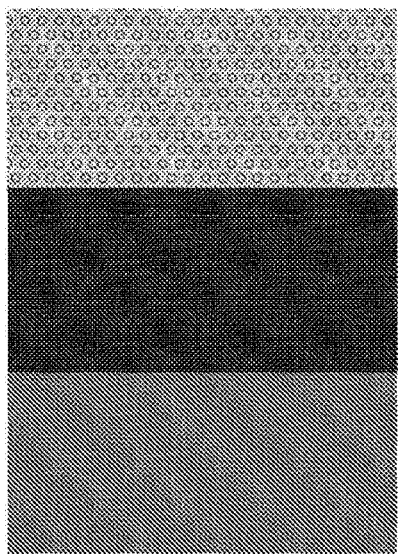
FIGS. 13A and 13B are microscopic images showing results obtained using Example 1.

FIG. 13A is an observation image of signal detection 3. The upper part of the image is a bright field image, the middle part is a Redmond Red fluorescence image, and the lower part is an FITC fluorescence image. As a result, fluorescence of Redmond Red was not observed, and fluorescence of FITC was observed across the entire field.

(Introduction of Sealing Solution)

100 µL of the sealing solution was introduced through the inlet port 122 of the fluidic device. As a result, the wells 141 were individually re-sealed, and sealed wells 142 were formed.

(Signal Detection 4)

Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of 5 seconds, and another fluorescence image was captured using the filter 2 at an exposure time of 1.5 seconds. Further, a bright field image of the same field was also captured.

Figure 13B:
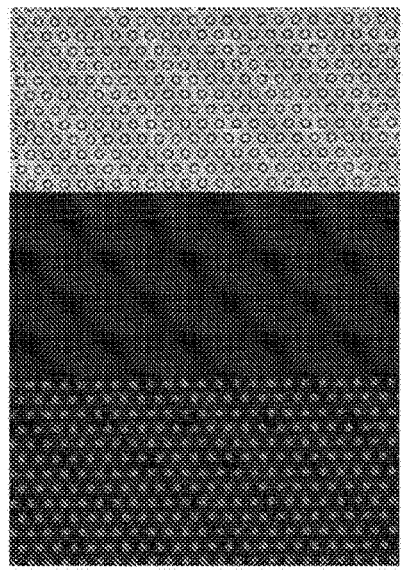

FIG. 13B is an observation image of signal detection 4. The upper part of the image is a bright field image, the middle part is a Redmond Red fluorescence image, and the lower part is an FITC fluorescence image. As a result, no fluorescence signal was observed in the Redmond Red fluorescence image, and fluorescence signals corresponding to the positions of the wells 142 were observed in the FITC fluorescence image.

Example 2

An experiment was performed under the same conditions as in Example 1 except that the second liquid did not contain Tween 20.

Figure 14A:
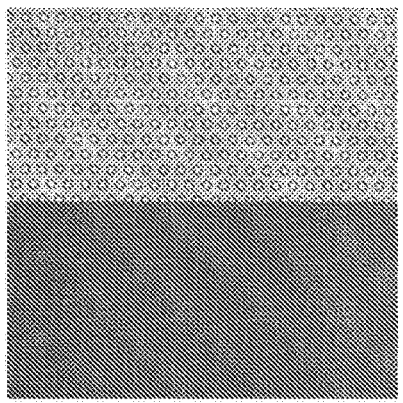
FIGS. 14A and 14B are microscopic images showing results obtained using Example 2.

FIG. 14A is an observation image of signal detection 1. The upper part of the image is a bright field image, and the lower part is a fluorescence image. As a result, fluorescence was observed across the entire field.

Figure 14B:
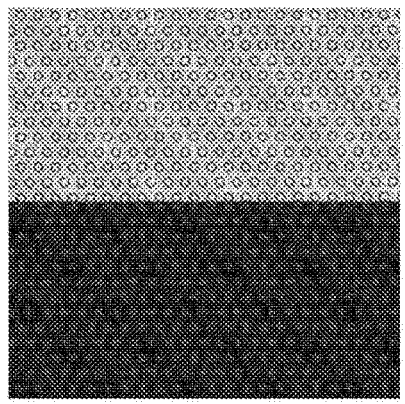

FIG. 14B is an observation image of signal detection 2. The upper part of the image is a bright field image, and the lower part is a fluorescence image. As a result, fluorescence signals corresponding to the positions of the wells 142 were observed. That is, it was found that the first liquid was accommodated in each of the plurality of wells 142.

Figure 15A:
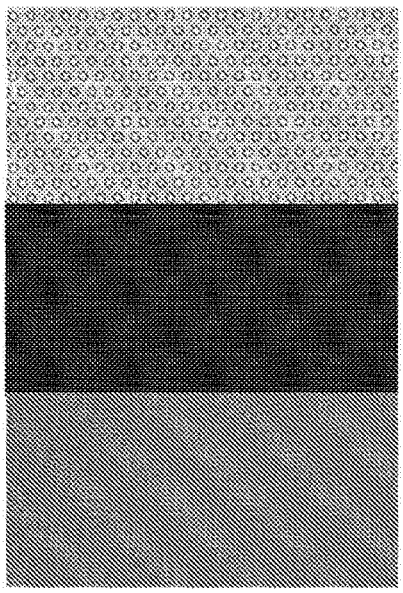
FIGS. 15A and 15B are microscopic images showing results obtained using Example 2.

FIG. 15A is an observation image of signal detection 3. The upper part of the image is a bright field image, the middle part is a Redmond Red fluorescence image, and the lower part is an FITC fluorescence image. As a result, fluorescence of Redmond Red was not observed, and fluorescence of FITC was observed across the entire field.

Figure 15B:
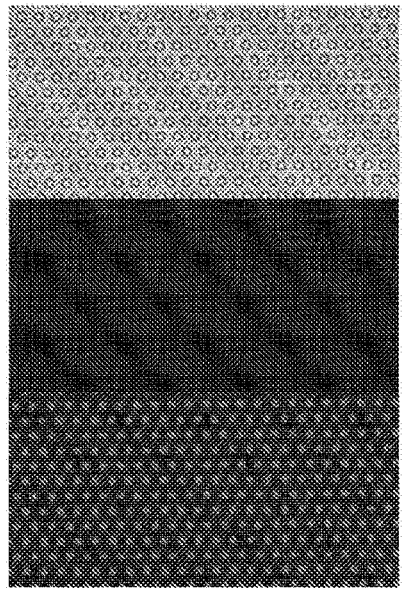

FIG. 15B is an observation image of signal detection 4. The upper part of the image is a bright field image, the middle part is a Redmond Red fluorescence image, and the lower part is an FITC fluorescence image. As a result, no fluorescence signal was observed in the Redmond Red fluorescence image, and fluorescence signals corresponding to the positions of the wells 142 were observed in the FITC fluorescence image.

Comparative Example 1

An experiment was performed under the same conditions as in Example 1 except that the first liquid did not contain Tween 20.

Comparative Example 2

An experiment was performed under the same conditions as in Example 1 except that the first liquid and the second liquid did not contain Tween 20.

Figure 16A:
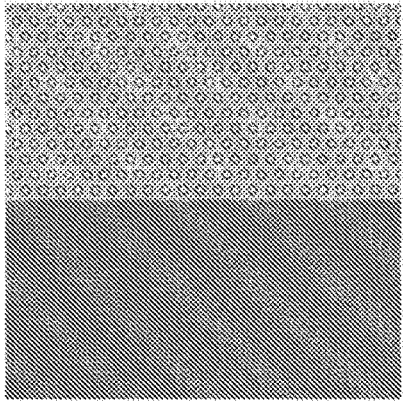
FIGS. 16A and 16B are microscopic images showing results obtained using Comparative Example 1.
Figure 17A:
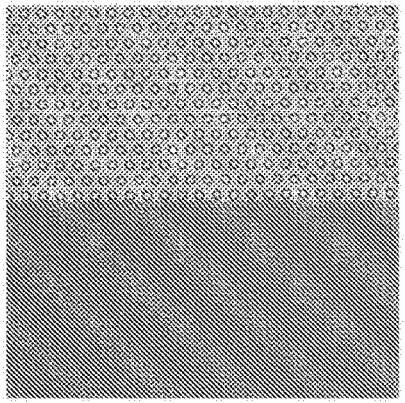
FIGS. 17A and 17B are microscopic images showing results obtained using Comparative Example 2.

FIG. 16A is an observation image of signal detection 1 according to Comparative Example 1. FIG. 17A is an observation image of signal detection 1 according to Comparative Example 2. The upper part of the image is a bright field image, and the lower part is a fluorescence image. As a result, fluorescence was observed across the entire field.

Figure 16B:
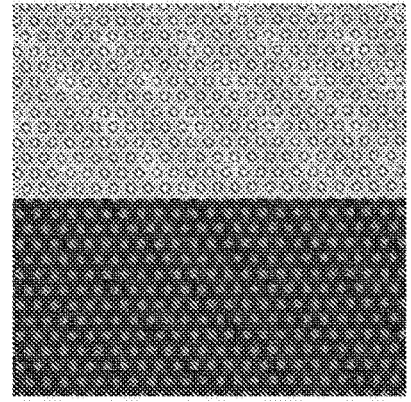
Figure 17B:
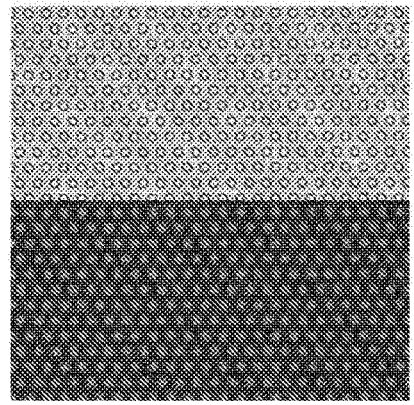

FIG. 16B is an observation image of signal detection 2 according to Comparative Example 1. FIG. 17B is an observation image of signal detection 2 according to Comparative Example 2. The upper part of the image is a bright field image, and the lower part is a fluorescence image. As a result, fluorescence signals corresponding to the positions of the wells 142 were observed. That is, it was found that the first liquid was accommodated in each of the plurality of wells 142.

Figure 18A:
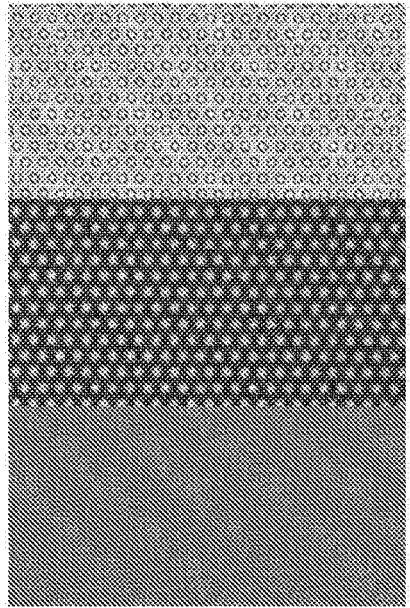
FIGS. 18A and 18B are microscopic images showing results obtained using Comparative Example 1.
Figure 19A:
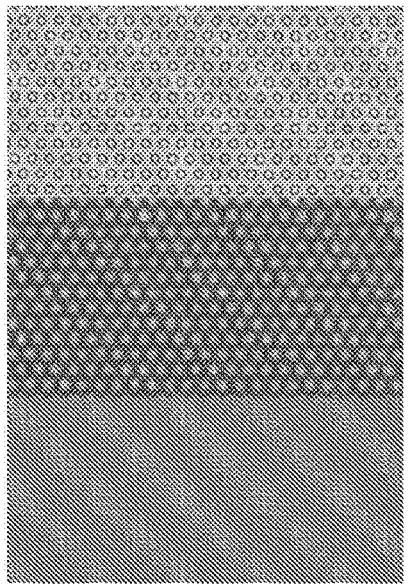
FIGS. 19A and 19B are microscopic images showing results obtained using Comparative Example 2.

FIG. 18A is an observation image of signal detection 3 according to Comparative Example 1. FIG. 19A is an observation image of signal detection 3 according to Comparative Example 2. The upper part of the image is a bright field image, the middle part is a Redmond Red fluorescence image, and the lower part is an FITC fluorescence image. As a result, Redmond Red fluorescence signals corresponding to the positions of the wells 142 were observed. That is, it was found that the first liquid was accommodated in each of the plurality of wells 142. Further, FITC fluorescence signals were observed across the entire field.

Figure 18B:
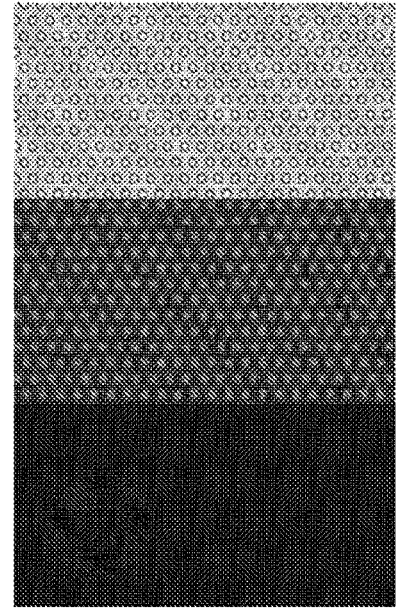
Figure 19B:
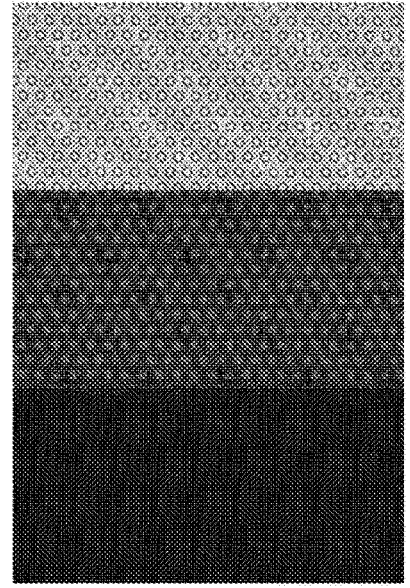

FIG. 18B is an observation image of signal detection 4 according to Comparative Example 1. FIG. 19B is an observation image of signal detection 4 according to Comparative Example 2. The upper part of the image is a bright field image, the middle part is a Redmond Red fluorescence image, and the lower part is an FITC fluorescence image. As a result, Redmond Red fluorescence signals corresponding to the positions of the wells 142 were observed. That is, it was found that the first liquid was accommodated in each of the plurality of wells 142. No fluorescence signal of FITC was observed.

As seen from the results of Examples 1 and 2 and Comparative Examples 1 and 2, liquid in the wells 141 can be replaced with the second liquid when the first liquid contains a surfactant, even when the first liquid accommodated in the respective wells is sealed with the sealing solution. It was found that liquid in the wells 141 can be replaced with the second liquid regardless of whether the second liquid contains a surfactant or not. Further, it was found that, liquid in the wells 141 cannot be replaced with the second liquid when the first liquid does not contain a surfactant, even when the second liquid contains a surfactant.

Example 3

The steps from (Introduction of First Liquid) to (Signal Detection 4) were performed in the same procedure as in Example 1. Subsequently, the following operations were performed.
(Introduction of Third Liquid)
20 μL of the third liquid was introduced through the inlet port 122 of the fluidic device.
(Signal Detection 5)
Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of ¼ second, and another fluorescence image was captured using the filter 2 at an exposure time of 1.5 seconds. Further, a bright field image of the same field was also captured.
(Introduction of Sealing Solution)
100 μL of the sealing solution was introduced through the inlet port 122 of the fluidic device. As a result, the wells 141 were individually re-sealed, and sealed wells 142 were formed.
(Signal Detection 6)
Then, using a fluorescence microscope, an image focusing on the wells 141 was taken via a surface on a side of the substrate 110 of the fluidic device 100 opposite to that on which the well array 140 was formed. In this process, the surface on a side of the substrate 110 opposite to that on which the well array 140 was formed was irradiated with excitation light. A fluorescence image was captured using the filter 1 at an exposure time of 5 seconds, and another fluorescence image was captured using the filter 2 at an exposure time of 1.5 seconds. Further, a bright field image of the same field was also captured.

Figure 20A:
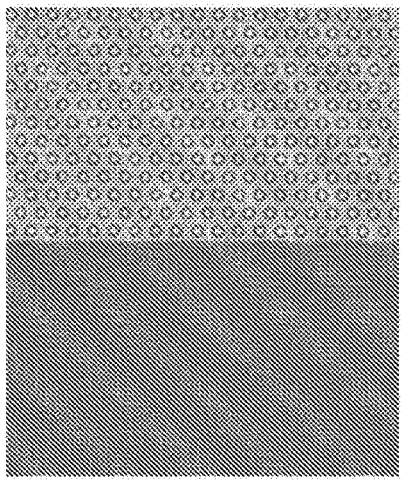
FIGS. 20A and 20B are microscopic images showing results obtained using Example 3.
Figure 20B:
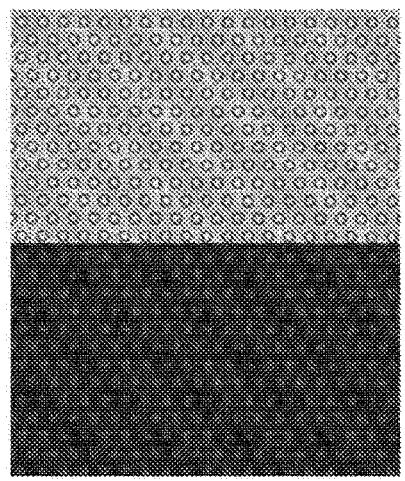

FIG. 20A is an observation image of signal detection 1. FIG. 20B is an observation image of signal detection 2. The upper part of the image is a bright field image, and the lower part is a fluorescence image.

Figure 21A:
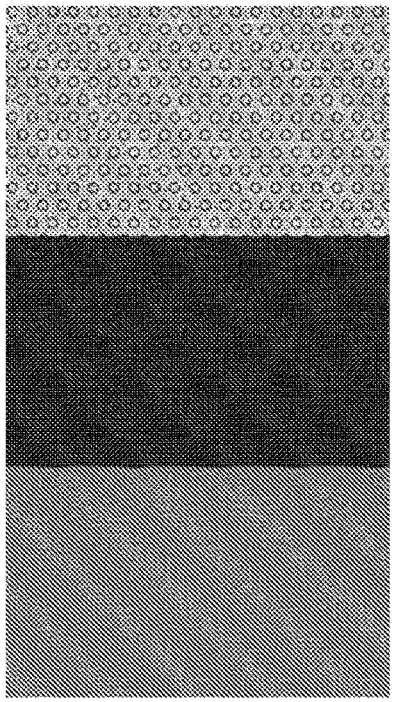
Figure 21B:
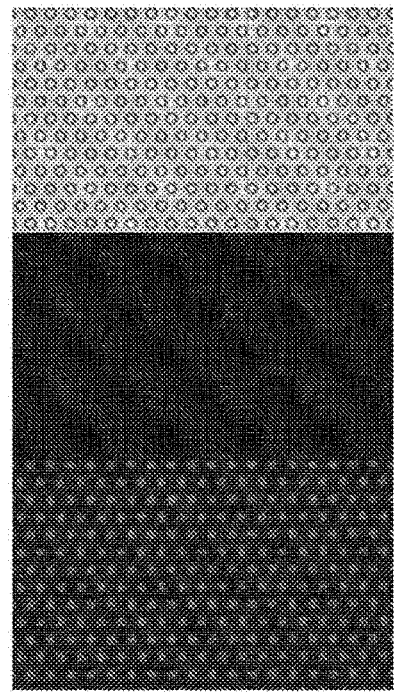

FIG. 21A is an observation image of signal detection 3. FIG. 21B is an observation image of signal detection 4. The upper part of the image is a bright field image, the middle part is a Redmond Red fluorescence image, and the lower part is an FITC fluorescence image.

As seen from the results of FIGS. 20A-B and 21A-B, the same results as in Example 1 were obtained.

Figure 22A:
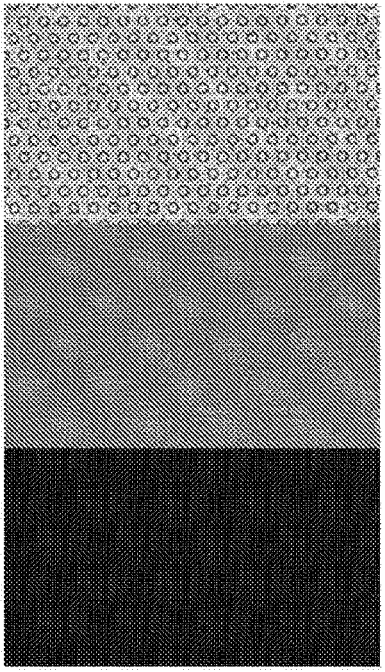
FIGS. 22A and 22B are microscopic images showing results obtained using Example 3.
Figure 22B:
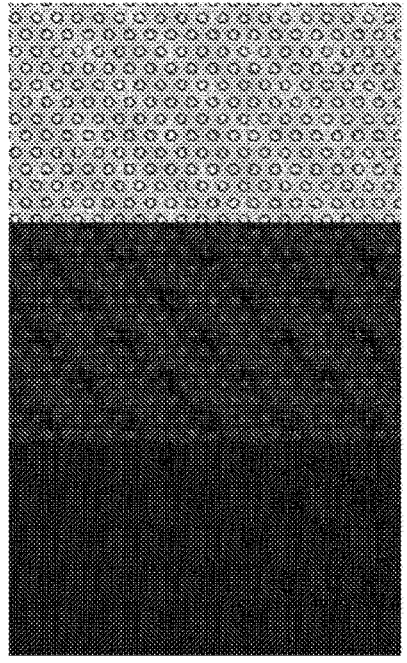

FIG. 22A is an observation image of signal detection 5. FIG. 22B is an observation image of signal detection 4. The upper part of the image is a bright field image, the middle part is a Redmond Red fluorescence image, and the lower part is an FITC fluorescence image.

As seen from the image of FIG. 22A, Redmond Red fluorescence signals were observed across the entire field. On the other hand, no fluorescence signal of FITC was observed. As seen from the image of FIG. 22B, Redmond Red fluorescence signals corresponding to the positions of the wells 142 were observed. That is, it was found that the third liquid was accommodated in each of the plurality of wells 142. On the other hand, no fluorescence signal of FITC was observed.

Example 4

An experiment was performed under the same conditions as in Example 3 except that the second liquid did not contain Tween 20.

Figure 23A:
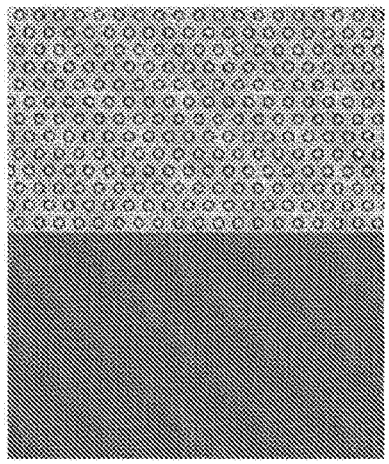
FIGS. 23A and 23B are microscopic images showing results obtained using Example 4.
Figure 23B:
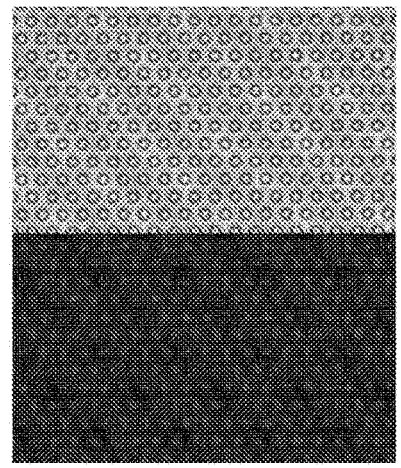

FIG. 23A is an observation image of signal detection 1. FIG. 23B is an observation image of signal detection 2. The upper part of the image is a bright field image, and the lower part is a fluorescence image.

Figure 24A:
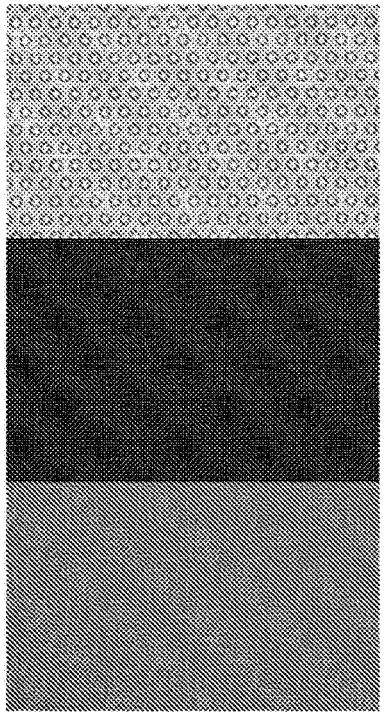
FIGS. 24A and 24B are microscopic images showing results obtained using Example 4.
Figure 24B:
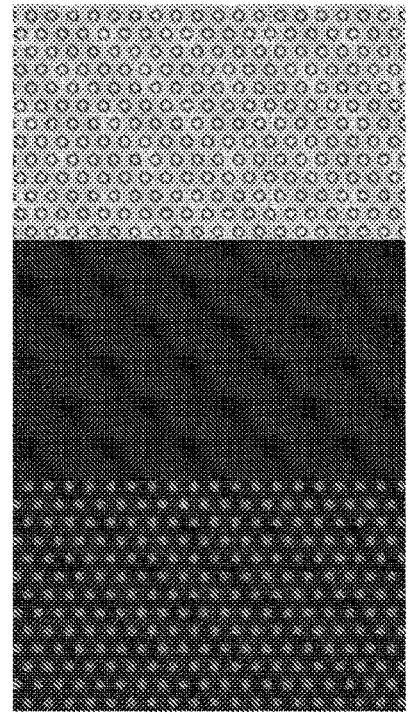

FIG. 24A is an observation image of signal detection 3. FIG. 24B is an observation image of signal detection 4. The upper part of the image is a bright field image, the middle part is a Redmond Red fluorescence image, and the lower part is an FITC fluorescence image.

As seen from the results of FIGS. 23 and 24, the same results as in Example 2 were obtained.

Figure 25A:
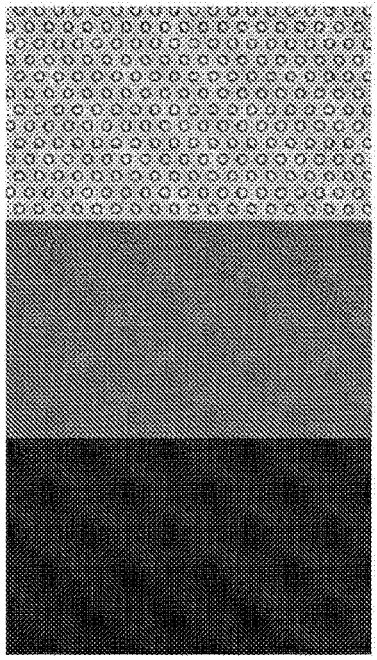
FIGS. 25A and 25B are microscopic images showing results obtained using Example 4.
Figure 25B:
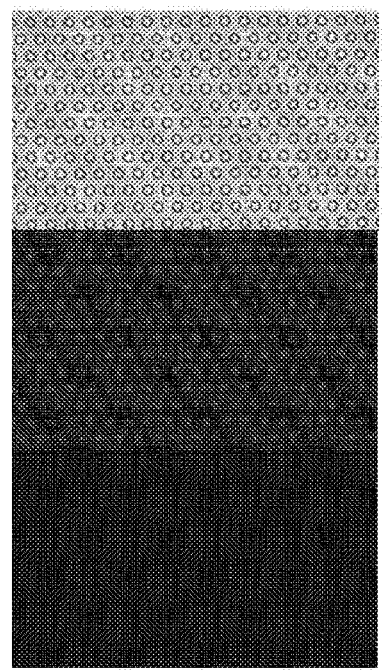

FIG. 25A is an observation image of signal detection 5. FIG. 25B is an observation image of signal detection 4. The upper part of the image is a bright field image, the middle part is a Redmond Red fluorescence image, and the lower part is an FITC fluorescence image.

As seen from the image of FIG. 25A, Redmond Red fluorescence signals were observed across the entire field. On the other hand, no fluorescence signal of FITC was observed. As seen from the image of FIG. 25B, Redmond Red fluorescence signals corresponding to the positions of the wells 142 were observed. That is, it was found that the third liquid was accommodated in each of the plurality of wells 142. On the other hand, no fluorescence signal of FITC was observed.

As seen from the above results, the steps of introducing a liquid containing a surfactant (in the present example, first liquid), sealing with the sealing solution, and introducing a final replacement liquid (in the present example, third liquid) are not required to be sequentially performed to accommodate the final replacement liquid in the wells. In other words, it was found that a final replacement liquid can be accommodated in the wells 141 when liquid containing a surfactant (in the present example, first liquid) is introduced into the wells 141 before the final replacement liquid is accommodated, even when liquid (in the present example, second liquid), which is introduced into the wells immediately before the final replacement liquid (in the present example, third liquid) is accommodated, does not contain a surfactant.

The reason for this seems to be that, since a surfactant is introduced into the wells 141 due to introduction of the first liquid, the surfactant may remain in the wells 141 or may be attached to an inner wall of the wells 141 even when liquid in the wells 141 is replaced with the second liquid containing no surfactant. Accordingly, when the third liquid is introduced, liquid in the wells 141 can be replaced with the third liquid due to an effect of the surfactant remaining in the wells 141.

Comparative Example 3

An experiment was performed under the same conditions as in Example 3 except that the first liquid did not contain Tween 20.

Figure 26A:
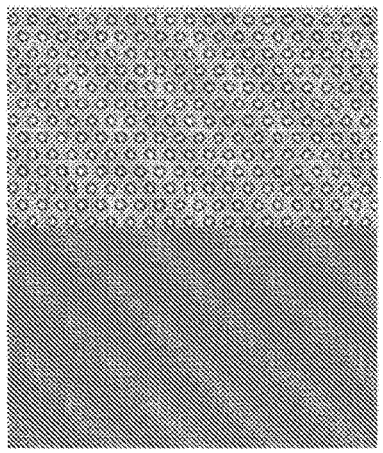
FIGS. 26A and 26B are microscopic images showing results obtained using Comparative Example 3.
Figure 26B:
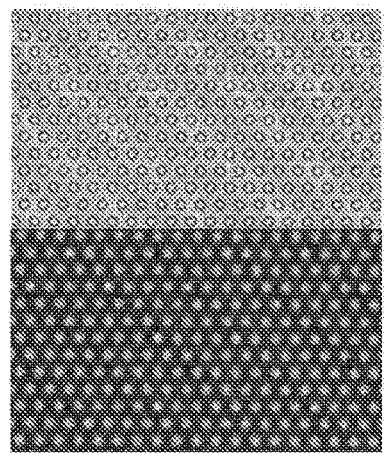

FIG. 26A is an observation image of signal detection 1. FIG. 26B is an observation image of signal detection 2. The upper part of the image is a bright field image, and the lower part is a fluorescence image. As seen from the results of FIG. 26, the same results as in Comparative Example 1 were obtained.

Figure 27A:
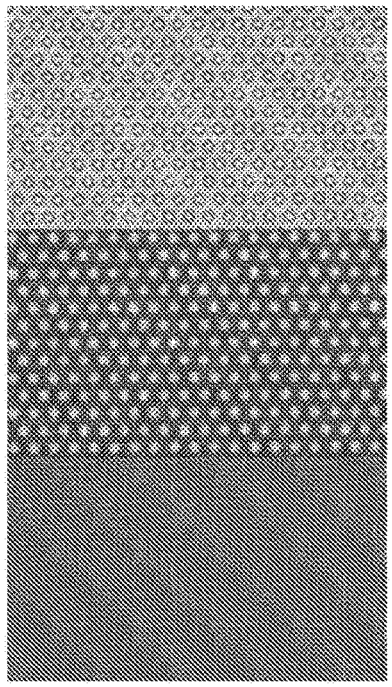
FIGS. 27A and 27B are microscopic images showing results obtained using Comparative Example 3.
Figure 27B:
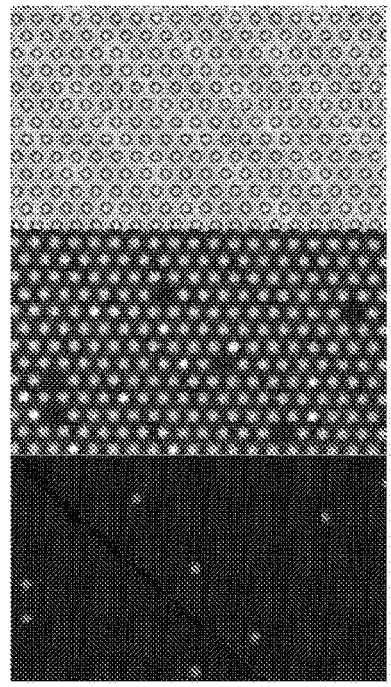

FIG. 27A is an observation image of signal detection 3. FIG. 27B is an observation image of signal detection 4. The upper part of the image is a bright field image, the middle part is a Redmond Red fluorescence image, and the lower part is an FITC fluorescence image. As seen from the image of FIG. 27A, the same results as in Comparative Example 1 were obtained. In the image of FIG. 27B, there are black voids, which correspond to some positions of the wells 142 in the Redmond Red fluorescence image. Since these positions of the black voids coincide with positions in the FITC fluorescence image where fluorescence signals are observed, it is found that replacement with the second liquid has occurred only in some of the wells 142. As described above, it is found that liquid in the wells 142 cannot be reliably replaced with the second liquid when the first liquid does not contain a surfactant.

Figure 28A:
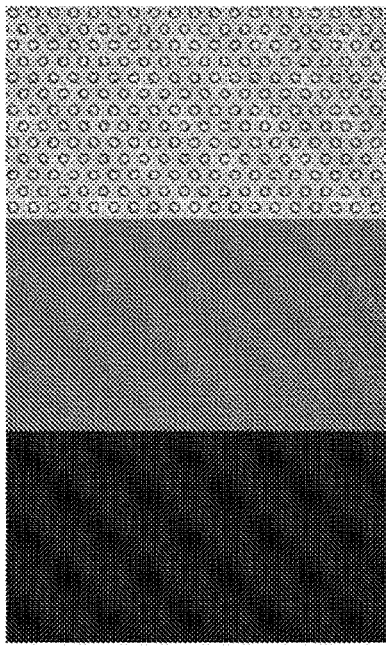
FIGS. 28A and 28B are microscopic images showing results obtained using Comparative Example 3.
Figure 28B:
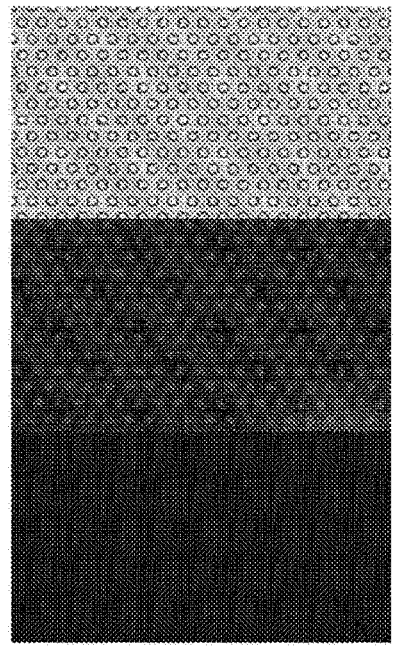

FIG. 28A is an observation image of signal detection 5. FIG. 28B is an observation image of signal detection 4. The upper part of the image is a bright field image, the middle part is a Redmond Red fluorescence image, and the lower part is an FITC fluorescence image.

As seen from the image of FIG. 28A, Redmond Red fluorescence signals were observed across the entire field. On the other hand, no fluorescence signal of FITC was observed. As seen from the image of FIG. 28B, Redmond Red fluorescence signals corresponding to the positions of the wells 142 were observed. That is, it was found that the third liquid was accommodated in each of the plurality of wells 142. On the other hand, no fluorescence signal of FITC was observed. That is, it was found that the second liquid accommodated in the wells 142 is replaced with the third liquid when the second liquid contains a surfactant.

Example 5

An experiment was performed under the same conditions as in Example 1 except that the material of the cover member 120 of the fluidic device was modified to glass.

Example 6

An experiment was performed under the same conditions as in Example 1 except that the material of the cover member 120 of the fluidic device was modified to polypropylene (manufactured by AS ONE Corporation, product number: PPN-051001).

Example 7

An experiment was performed under the same conditions as in Example 1 except that the material of the cover member 120 of the fluidic device was modified to silicone (Togawa Rubber Co., Ltd., product number: K-125(50)).

Comparative Example 4

An experiment was performed under the same conditions as in Example 5 except that the first liquid and the second liquid did not contain a surfactant.

Comparative Example 5

An experiment was performed under the same conditions as in Example 6 except that the first liquid and the second liquid did not contain a surfactant.

Comparative Example 6

An experiment was performed under the same conditions as in Example 7 except that the first liquid and the second liquid did not contain a surfactant.

Figure 29A:
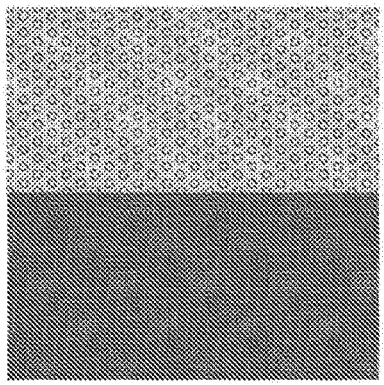
FIGS. 29A and 29B are microscopic images showing results obtained using Example 5.
Figure 29B:
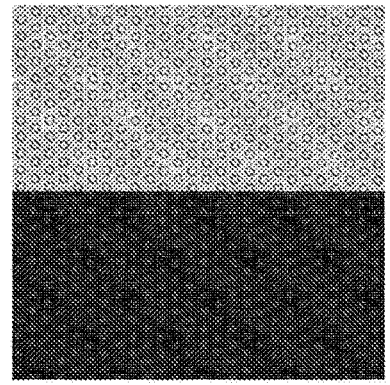
Figure 31A:
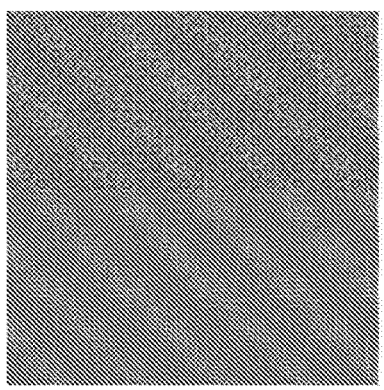
FIGS. 31A and 31B are microscopic images showing results obtained using Example 6.
Figure 31B:
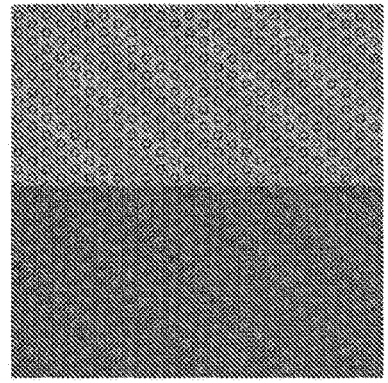
Figure 33A:
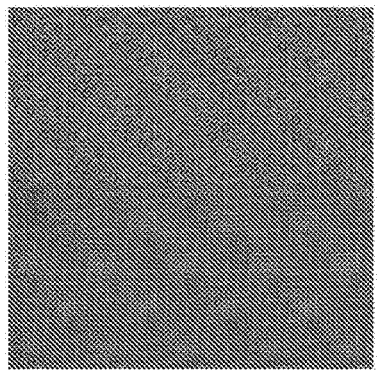
FIGS. 33A and 33B are microscopic images showing results obtained using Example 7.
Figure 33B:
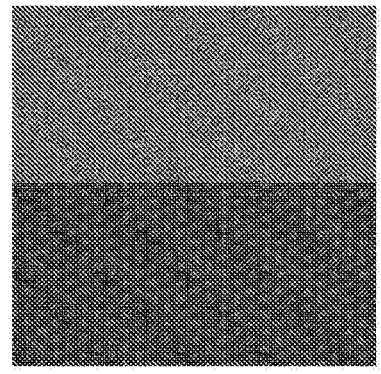

FIG. 29A is an observation image of signal detection 1 according to Example 5. FIG. 29(b) is an observation image of signal detection 2 according to Example 5. FIG. 31A is an observation image of signal detection 1 according to Example 6. FIG. 31B is an observation image of signal detection 2 according to Example 6. FIG. 33A is an observation image of signal detection 1 according to Example 7. FIG. 33B is an observation image of signal detection 2 according to Example 7. The upper part of the image is a bright field image, and the lower part is a fluorescence image.

Figure 30A:
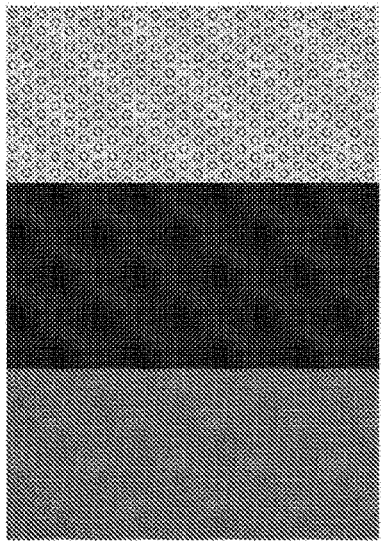
FIGS. 30A and 30B are microscopic images showing results obtained using Example 5.
Figure 30B:
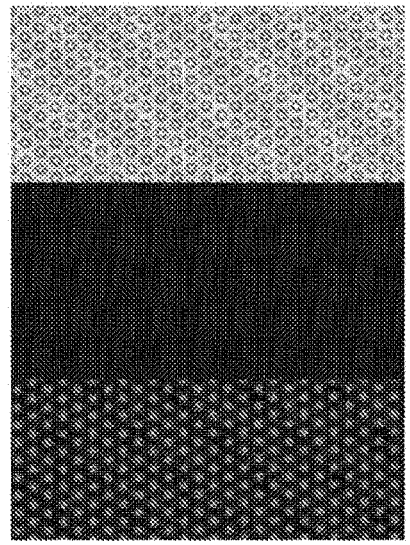
Figure 32A:
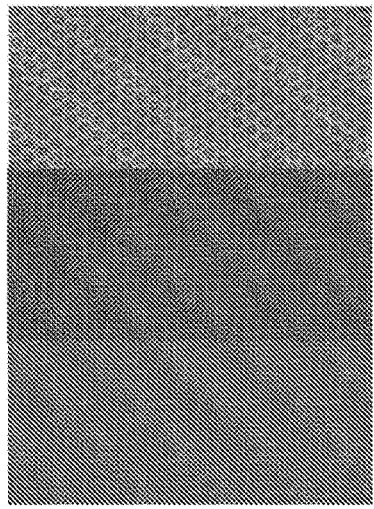
FIGS. 32A and 32B are microscopic images showing results obtained using Example 6.
Figure 32B:
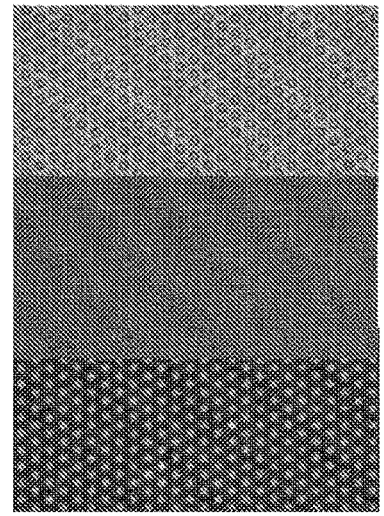
Figure 34A:
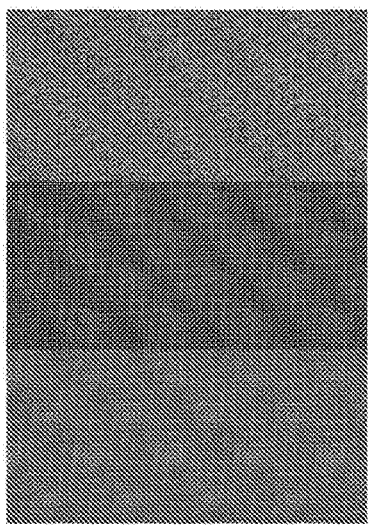
FIGS. 34A and 34B are microscopic images showing results obtained using Example 7.
Figure 34B:
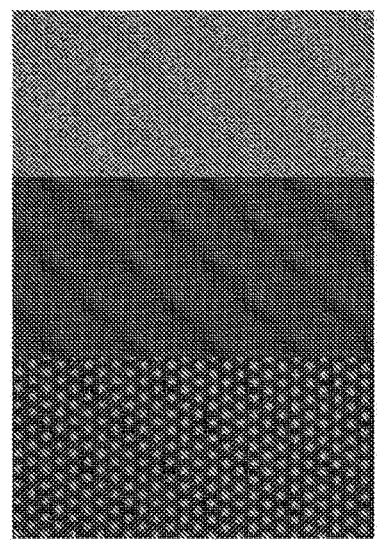

FIG. 30A is an observation image of signal detection 3 according to Example 5. FIG. 30B is an observation image of signal detection 4 according to Example 5. FIG. 32A is an observation image of signal detection 3 according to Example 6. FIG. 32B is an observation image of signal detection 4 according to Example 6. FIG. 34A is an observation image of signal detection 3 according to Example 7. FIG. 34B is an observation image of signal detection 4 according to Example 7. The upper part of the image is a bright field image, the middle part is a Redmond Red fluorescence image, and the lower part is an FITC fluorescence image.

As seen from the results of FIGS. 29A-B to 34A-B, the same results as in Example 1 were obtained in Examples 5 to 7. That is, it is found that the first liquid in the wells 142 that are individually sealed with the sealing solution can be replaced with the second liquid when the first liquid contains a surfactant, even when the cover member 120 of the fluidic device is made of glass, polypropylene, or silicone.

Figure 35A:
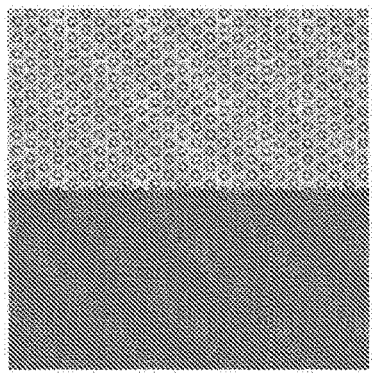
FIGS. 35A and 35B are microscopic images showing results obtained using Comparative Example 4.
Figure 35B:
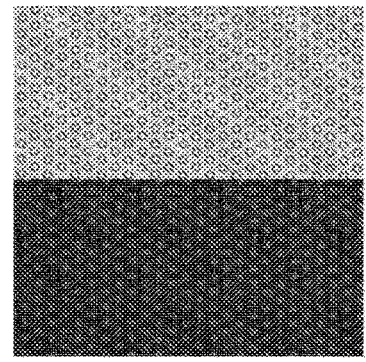
Figure 37A:
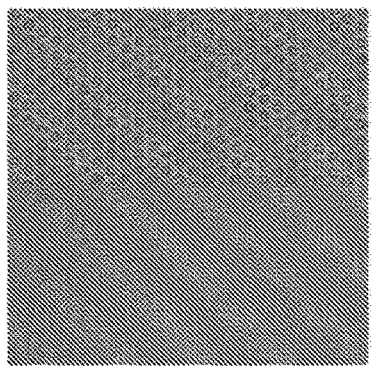
FIGS. 37A and 37B are microscopic images showing results obtained using Comparative Example 5.
Figure 37B:
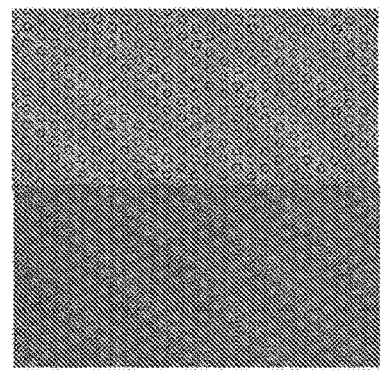
Figure 39A:
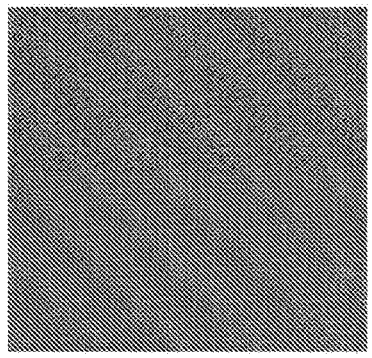
FIGS. 39A and 39B are microscopic images showing results obtained using Comparative Example 6.
Figure 39B:
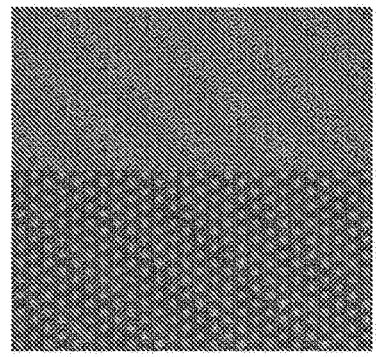

FIG. 35A is an observation image of signal detection 1 according to Comparative Example 4. FIG. 35B is an observation image of signal detection 2 according to Comparative Example 4. FIG. 37A is an observation image of signal detection 1 according to Comparative Example 5. FIG. 37B is an observation image of signal detection 2 according to Comparative Example 5. FIG. 39A is an observation image of signal detection 1 according to Comparative Example 6. FIG. 39B is an observation image of signal detection 2 according to Comparative Example 6. The upper part of the image is a bright field image, and the lower part is a fluorescence image.

Figure 36A:
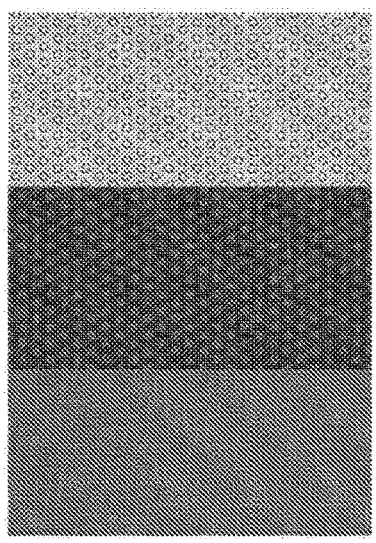
FIGS. 36A and 36B are microscopic images showing results obtained using Comparative Example 4.
Figure 36B:
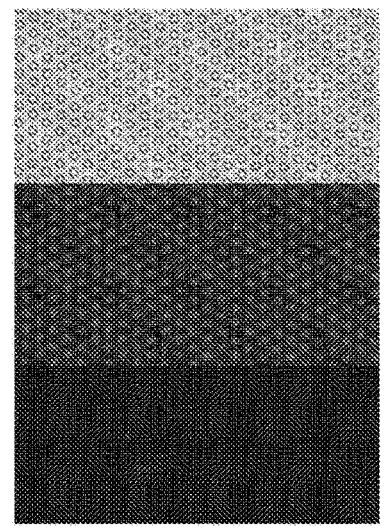
Figure 38A:
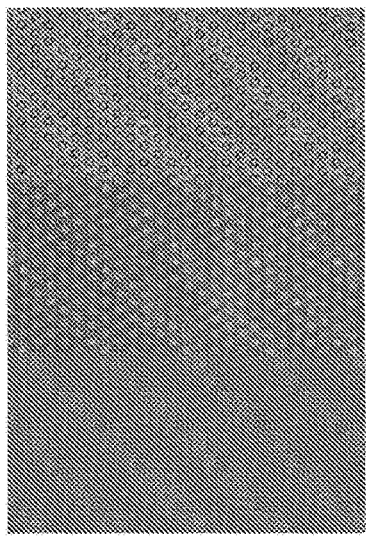
FIGS. 38A and 38B are microscopic images showing results obtained using Comparative Example 5.

FIG. 36A is an observation image of signal detection 3 according to Comparative Example 4. FIG. 36B is an observation image of signal detection 4 according to Comparative Example 4. FIG. 38A is an observation image of signal detection 3 according to Comparative Example 5.

Figure 38B:
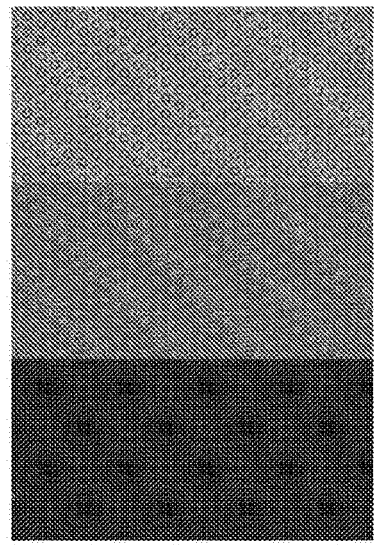
Figure 40A:
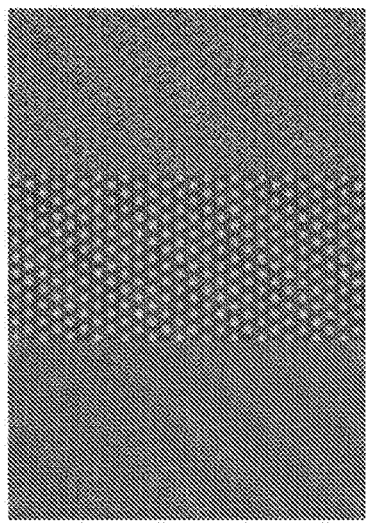
FIGS. 40A and 40B are microscopic images showing results obtained using Comparative Example 6.
Figure 40B:
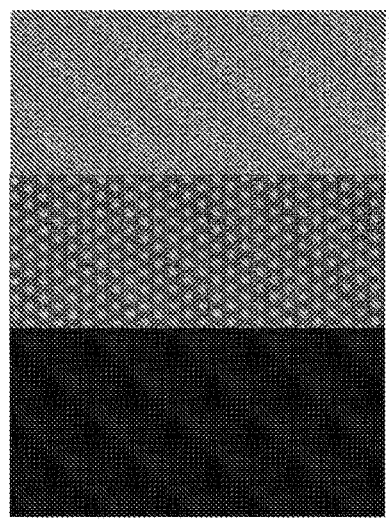

FIG. 38B is an observation image of signal detection 4 according to Comparative Example 5. FIG. 40A is an observation image of signal detection 3 according to Comparative Example 6. FIG. 40B is an observation image of signal detection 4 according to Comparative Example 6. The upper part of the image is a bright field image, the middle part is a Redmond Red fluorescence image, and the lower part is an FITC fluorescence image.

As seen from the results of FIGS. 35 to 40, the same results as in Comparative Example 2 were obtained in Comparative Examples 4 to 6. That is, it is found that the first liquid in the wells 142 that are individually sealed with the sealing solution cannot be replaced with the second liquid when the first liquid contains no surfactant, even when the cover member 120 of the fluidic device is made of glass, polypropylene, or silicone.

The present application addresses the following. In digital quantification technology, a reaction reagent in which target molecules are mixed are divided into a large number of micro compartments using a sealing solution or a lipid bilayer. Then, a reaction is individually performed in the respective micro compartments to detect a target molecule. For this reason, the analysis results that can be obtained are usually limited to those according to the reaction reagent contained in the micro compartments. An aspect of the present invention is to provide a technique for replacing a liquid in the individually sealed micro compartments.

The present invention includes the following aspects.

[1] A method of introducing a second liquid into wells in a fluidic device which includes a substrate and a plurality of the wells, the wells being open to a first surface of the substrate and accommodating a first liquid containing a surfactant, and openings of the wells being sealed with a first sealing solution supplied onto the first surface, the method including: introducing the second liquid onto the first surface, whereby the first sealing solution is replaced with the second liquid.

[2] The method according to the above [1], further including: introducing a second sealing solution into the fluidic device after the step of introducing the second liquid, whereby the openings of the plurality of wells are sealed with the second sealing solution supplied onto the first surface with the second liquid or a mixture of the first liquid and the second liquid being accommodated in the wells.

[3] The method according to the above [1] or [2], further including before the step of introducing the second liquid: introducing the first liquid into the fluidic device; and introducing the first sealing solution into the fluidic device to seal the openings of the plurality of wells with the first sealing solution supplied onto the first surface with the first liquid being accommodated in the wells.

[4] The method according to any one of the above [1] to [3], wherein the first liquid and the second liquid are miscible with each other.

[5] The method according to any one of the above [1] to [4], wherein the fluidic device further includes a cover member disposed to face the first surface, and a space between the cover member and the first surface forms a flow path.

[6] The method according to the above [5], wherein the second liquid is introduced into the fluidic device through the flow path.

[7] The method according to any one of the above [1] to [6], wherein the first liquid and the second liquid contain a reaction reagent.

[8] The method according to any one of the above [1] to [7], wherein at least part of components contained in the first liquid remains in the wells after the second liquid is introduced into the wells.

[9] The method according to the above [8], wherein at least part of components contained in the first liquid is held by a carrier and remains in the wells.

[10] The method according to any one of the above [1] to [9], wherein an affinity between the first surface and the first sealing solution is substantially the same or lower than affinity between the first surface and the second liquid.

[11] The method according to the above [10], wherein the first surface is made of a cycloolefin polymer, the first liquid and the second liquid contain water as a main component, and the first sealing solution is a fluorine-based oil.

According to the present invention, a technique for replacing liquid in the individually sealed micro compartments can be provided.

INDUSTRIAL APPLICABILITY

According to the present invention, a technique for replacing liquid in the individually sealed micro compartments can be provided.

REFERENCE SIGNS LIST 100, 200 . . . Fluidic device
110 . . . Substrate
111 . . . First surface
120 . . . Cover member
121 . . . Projection
122 . . . Inlet port
123 . . . Discharge port
130 . . . Flow path
140 . . . Well array
141 . . . Well
142 . . . Sealed well (micro compartments)
210 . . . Wall member
L110 . . . First liquid
L120, L620 . . . Sealing solution
L410 . . . Second liquid Obviously, numerous modifications and variations of the present invention are possible in light of the above teachings. It is therefore to be understood that within the scope of the appended claims, the invention may be practiced otherwise than as specifically described herein.

What is claimed is:

1. A method of replacing liquids, comprising:
introducing a first liquid including a surfactant into a fluidic device such that the first liquid is accommodated in a plurality of wells formed in a substate of the fluidic device;
introducing a sealing solution into the fluidic device such that the sealing solution is introduced into a flow path of the fluidic device and seals the first liquid in the plurality of wells; and
introducing a second liquid into the fluidic device such that the second liquid flushes out the sealing solution entirely from the flow path of the fluidic device and replaces the sealing solution introduced into the flow path of the fluidic device and is introduced into the plurality of wells in which the first liquid is accommodated.

2. The method according to claim 1, further comprising:
introducing a second sealing solution into the fluidic device after the introducing of the second liquid such that the second sealing solution seals openings of the wells and that the second liquid or a mixture of the first liquid and the second liquid are accommodated in the wells.

3. The method according to claim 1, wherein the first liquid includes the surfactant in a concentration in a range of 0.001 v/v % to 1.0 v/v %.

4. The method according to claim 1, wherein the first liquid and the second liquid are miscible with each other.

5. The method according to claim 1, wherein the fluidic device further includes a cover positioned to face the plurality of wells formed in the substrate such that the flow path is formed in a space between the cover and the plurality of wells.

6. The method according to claim 1, wherein each of the first liquid and the second liquid includes a main component comprising water, and the sealing solution comprises a fluorine-based oil.

7. The method according to claim 1, wherein each of the first liquid and the second liquid include a reaction reagent.

8. The method according to claim 1, wherein the second liquid retains at least one component of the first liquid in the wells after the introducing of the second liquid.

9. The method according to claim 8, wherein the at least one component of the first liquid is held by a carrier and remains in the wells.

10. The method according to claim 1, wherein the substrate of the fluidic device has a surface in which the plurality of wells is formed such that the sealing solution has an affinity which is substantially the same as or lower than an affinity between the surface of the substrate and the second liquid.

11. The method according to claim 10, wherein the surface of the substrate in the fluidic device comprises a cycloolefin polymer, each of the first liquid and the second liquid includes a main component comprising water, and the sealing solution comprises a fluorine-based oil.

12. The method according to claim 1, wherein the first liquid includes a carrier and a target molecule held by the carrier.

13. The method according to claim 1, further comprising:
preparing the fluidic device by including in the plurality of wells of the fluidic device a carrier that captures a target molecule in the first fluid.

14. The method according to claim 1, wherein the first liquid includes the surfactant in a concentration in a range of 0.005 v/v % to 0.5 v/v %.

15. The method according to claim 1, wherein the first liquid includes the surfactant in a concentration in a range of 0.01 v/v % to 0.1 v/v %.

16. The method according to claim 2, wherein the substrate of the fluidic device has a surface in which the plurality of wells is formed such that the sealing solution has an affinity which is substantially the same as or lower than an affinity between the surface of the substrate and the second liquid.

17. The method according to claim 16, wherein the surface of the substrate in the fluidic device comprises a cycloolefin polymer, each of the first liquid and the second liquid includes a main component comprising water, and the sealing solution comprises a fluorine-based oil.

18. The method according to claim 3, wherein the substrate of the fluidic device has a surface in which the plurality of wells is formed such that the sealing solution has an affinity which is substantially the same as or lower than an affinity between the surface of the substrate and the second liquid.

19. The method according to claim 18, wherein the surface of the substrate in the fluidic device comprises a cycloolefin polymer, each of the first liquid and the second liquid includes a main component comprising water, and the sealing solution comprises a fluorine-based oil.

20. The method according to claim 4, wherein the substrate of the fluidic device has a surface in which the plurality of wells is formed such that the sealing solution has an affinity which is substantially the same as or lower than an affinity between the surface of the substrate and the second liquid.

* * * * *